US012741994B2

(12) United States Patent
Sato et al.

(10) Patent No.: US 12,741,994 B2
(45) Date of Patent: Sep. 22, 2026

(54) PEPTIDE HAVING PLANT STEM CELL-INDUCING EFFECT AND PLANT PEST RESISTANCE-INDUCING EFFECT

(71) Applicants: KYOTO PREFECTURAL PUBLIC UNIVERSITY CORPORATION, Kyoto (JP); KYOTO SANGYO UNIVERSITY, Kyoto (JP)

(72) Inventors: Masahiko Sato, Kyoto (JP); Issei Ohshima, Kyoto (JP); Tomoko Hirano, Kyoto (JP); Seisuke Kimura, Kyoto (JP)

(73) Assignees: KYOTO PREFECTURAL PUBLIC UNIVERSITY CORPORATION, Kyoto (JP); KYOTO SANGYO UNIVERSITY, Kyoto (JP)

( * ) Notice: Subject to any disclaimer, the term of this patent is extended or adjusted under 35 U.S.C. 154(b) by 327 days.

(21) Appl. No.: 18/025,541

(22) PCT Filed: Sep. 16, 2021

(86) PCT No.: PCT/JP2021/034176

§ 371 (c)(1),
(2) Date: Mar. 9, 2023

(87) PCT Pub. No.: WO2022/059746

PCT Pub. Date: Mar. 24, 2022

(65) Prior Publication Data

US 2024/0067682 A1 Feb. 29, 2024

(30) Foreign Application Priority Data

Sep. 17, 2020 (JP) ................................ 2020-156361

(51) Int. Cl.
*C07K 14/435* (2006.01)
*C12N 15/82* (2006.01)

(52) U.S. Cl.
CPC .... *C07K 14/43563* (2013.01); *C12N 15/8262* (2013.01)

(58) Field of Classification Search
None
See application file for complete search history.

(56) References Cited

U.S. PATENT DOCUMENTS

2009/0300802 A1 12/2009 Ryan et al.
2017/0332645 A1 11/2017 Chen et al.

FOREIGN PATENT DOCUMENTS

| | | | |
|---|---|---|---|
| CN | 1610556 | A | 4/2005 |
| JP | 2012187040 | A | 10/2012 |
| JP | 2015208256 | A | 11/2015 |
| WO | 2002070665 | A2 | 9/2002 |
| WO | 2002070665 | A3 | 11/2004 |

OTHER PUBLICATIONS

Chen et al., Quantitative Peptidomics Study Reveals That a Wound-Induced Peptide from PR-1 Regulates Immune Signaling in Tomato, 2014, The Plant Cell, vol. 26, pp. 4135-4148 (Year: 2014).*

GenBank: AY117187.1, Arabidopsis thaliana putative pathogenesis-related PR-1 protein (At2g14610) mRNA, complete cds, Sep. 18, 2002 (Year: 2002).*

Chen et al., "Quantitative Peptidomics Study Reveals That a Wound-Induced Peptide from PR-1 Regulates Immune Signaling in Tomato", The Plant Cell, 2014, vol. 26, No. 10, pp. 4135-4148.

Aparecido et al., "B-cell linear epitopes mapping of antigen-5 allergen from *Polybia paulista* wasp venom", Journal of Allergy and Clinical Immunology, Letter to the Editor, 2014, vol. 135, No. 1, 12 pages.

Chien et al., "A salt-regulated peptide derived from the CAP superfamily protein negatively regulates salt-stress tolerance in *Arabidopsis*", Journal of Experimental Botany, 2015, vol. 66, No. 17, pp. 5301-5313.

Akbudak et al., "Pathogenesis related protein-I (PR-1) genes in tomato (*Solanum lycopersicum* L.): Bioinformatics analyses and expression profiles in response to drought stress", Genomics, 2020, vol. 112, No. 6, pp. 4089-4099.

Supplementary Extended European Search Report dated Sep. 16, 2024 for corresponding EP patent application No. 21869429.7, 11 pages.

International Search Report for International Application No. PCT/JP2021/034176 dated Nov. 16, 2021, 8 pages including English translation.

Tabata et al., "CAP (Cysteine-rich secretory proteins, Antigen 5, and Pathogenesis-related 1 protein) superfamily protein [*Arabidopsis thaliana*]", Database DDB J/EMBUGenBank [online], Feb. 14, 2019, Accession No. NP _197985, https:// www.ncbi.nlm.nih.gov/protein/NP _197985.

Hirano et al. "Reprogramming of the Developmental Program of Rhus javanica During Initial Stage of Gall Induction by Schlechtendalia chinensis", Frontiers in Plant Science, 2020, vol. 11, Article 471, pp. 1-13.

Takeda et al., "Comparative transcriptome analysis of galls from four different host plants suggests the molecular mechanism of gall development", PLOS ONE, 2019, vol. 14, No. 10., pp. 1-19.

(Continued)

*Primary Examiner* — Amjad Abraham
*Assistant Examiner* — Christina L Meadows
(74) *Attorney, Agent, or Firm* — MH2 Technology Law Group, LLP

(57) ABSTRACT

Disclosed are a partial peptide of cysteine-rich secretory protein, antigen 5, and pathogenesis-related 1 (CAP), consisting of an amino acid sequence of the conserved region of CAP, the peptide having at least one effect selected from the following effects: a plant stem cell-inducing effect, a plant environmental stress tolerance-enhancing effect, a plant pest resistance-inducing effect, a germination-promoting effect, a plant transformation efficiency-enhancing effect, and a plant growth-promoting effect; and a plant stem cell inducer, an environmental stress enhancer, a plant pest resistance inducer, a germination promoter, a transformation efficiency enhancer, and a plant growth promoter, all of which comprise the peptide.

19 Claims, 7 Drawing Sheets

Specification includes a Sequence Listing.

(56) References Cited

OTHER PUBLICATIONS

Office Action dated Feb. 10, 2026 for corresponding Japanese Application No. 2022-550609, 6 pages (with translation).

Estrella et al., “Characterization of toxins from the broad-banded water snake *Helicops angulatus* (Linnaeus, 1758): isolation of a cysteine-rich secretory protein, Helicopsin”, Arch Toxicol, 2011, vol. 85, pp. 305-313.

Unknown Author, Office Action dated Jun. 26, 2026 for corresponding Chinese Application No. 202180054664.4, 14 pages with machine English translation.

* cited by examiner

Fig. 1

```
            ..........210.......220.......230.......240.......250
CrCAP2562   ----------VL NCGHFTQIEW KNTKELGIGS AKGKS----G KLYVVANYNP
Be45393-432 ----------VL TCGHFTQIVW KETKELGIGS AKSKS----G KLYVVANYKP
Sc8480      --------RTR EINQFTQIVW QNTKKIGVEI INEDN----V -ILVLVIYSP
AT1G50050   --------GAQ QCKHYTQVVW SNSVKIGCAR VLCNN----G GYFVGCNYDA
Cc45036     --------GLK AVGHYTQMVW ATTHKVGCGV SKCLGGEWGT FYNYVCNYCP
AT5G02730   --------SGA MCGHYTQIVW RTTTAVGCAR SKCDN---NE GFLVICEYSP
At1g01310   --------RQH MCGHYTQIVW RDSTKVGCAS VDCEN---G- GVYAICVYNP
At5g57625   --------RSG MCGHYTQMVW RDTKRLGCAR VVCEN---GA GVFITCNYDP
At4g25790   --------RDG MCGHYTQIVW KETRRLGCAR VVCEN---GA GVFITCNYDP
At4g25780   --------AGQ MCGHYTQIVW KSTRKVGCAR VVCDN---G- GIFMTCNYDP
At3g09590   --------PGK MCGHYTQMVW RETTAVGCAR VKCHN---GR GYLVVCEYDP
At4g31470   --------ANG DCLHYTQLVW KKSSRIGCAI SFCKT---G- DTFIICNYDP
AT5G66590   --------ANH TCGVYKQVVW RNSKELGCAQ ATCTK---ES TVLTICFYNP
At4g30320   ---------SE MCGHYTQIVW KNTQKIGCAR VICNG---GQ GVFLTCNYDP
AT1G50060   --------RGK QCLHYTQVVW RDSVKIGCAR VQCTN---T- NNFVSCNYNS
At3g19690   ------RRNGG TCLHYTQVVW KNTVRLGCAK VVCNS---G- GTFITCNYDP
At4g33720   --------NDK QCGHYTQVVW RNSERLGCAK VRCNN---G- GTFITCNYDP
At5g26130   --------RGK QCGHYTQVVW RTSEWVGCAK VKCDN---G- GTFVTCNYYP
AT4G33710   --------AGK QCGHYTQVVW KNSEWVGCAK VKCDN---G- GTFVTCNYSH
AT4G07820   --------AGK SCDGYKQVLF RKSVFLGCAK VKCNN---G- GFLAICSYDP
AT2G19970   ---------KD VCGHYTQMVA NQSLSLGCGS FRCHE---NE LIYIVCNYYP
AT4G33730   ---------GP ACGHYTQVVW RGSARLGCGK AKC-N---NG ASIVVCNYDP
AT2G19980   ---------SE PCGHYTQIWA NQSTKLGCGT VRCFK---NE YVWVVCNYAP
Sc29472     ---------EN DAYHFTQIVW KKTTRVGFAL LFKKS----- TTYFSALYEP
Cc49380-9   ---------GK LLCWLCTQEL KRA--LARTQ R--------S RAHDKHRNRN
Sc3713      ---NKPKLFE KTHPFTQVVW KSTTNIGVGI LIVN-----N TVNVMVIYSP
Sc9417      NKPKPVPIKT LPMEFAQIVW KATKKIGVGK VTNN-----N LTLVVAIYDP
Sc45535     ---------SA TADSFTQVVW ESTEKLGASI MTKS-----G VLGVVVFYYP
Consistency 0010000143 4646888787 6574489664 6353400031 3456565947
```

Fig. 2

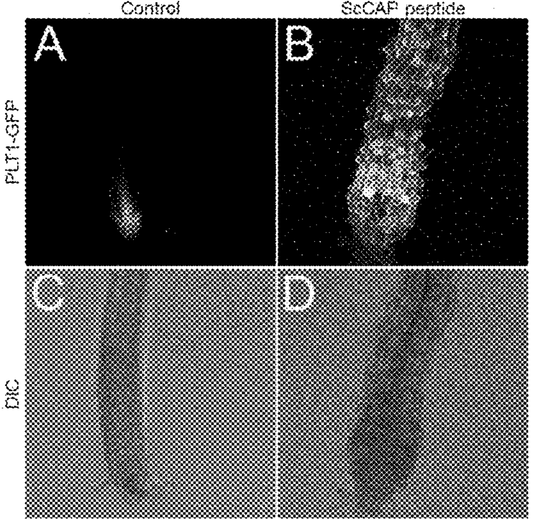

SEQUENCE LISTING

```
<160> NUMBER OF SEQ ID NOS: 21

<210> SEQ ID NO 1
<211> LENGTH: 22
<212> TYPE: PRT
<213> ORGANISM: Artificial Sequence
<220> FEATURE:
<223> OTHER INFORMATION: partial peptide of CAP

<400> SEQUENCE: 1

Thr Gln Val Val Trp Lys Ser Thr Thr Asn Ile Gly Val Gly Ile Leu
1               5                   10                  15

Ile Val Asn Gly Thr Val
            20


<210> SEQ ID NO 2
<211> LENGTH: 166
<212> TYPE: PRT
<213> ORGANISM: Arabidopsis thaliana

<400> SEQUENCE: 2

Met Lys Met Phe Lys Ser Pro Gln Thr Leu Ile Leu Ser Val Ile Val
1               5                   10                  15

Leu Phe Leu Ala Phe Ala Val Pro Leu Lys Ala Gln Asp Gln Pro Gln
            20                  25                  30

Asp Tyr Leu Asp Glu His Asn Arg Ala Arg Thr Gln Val Gly Val Pro
        35                  40                  45

Pro Met Lys Trp His Ala Gly Ala Glu Gln Tyr Ala Trp Asn Tyr Ala
    50                  55                  60

Gln Gln Arg Lys Gly Asp Cys Ser Leu Thr His Ser Asn Ser Asn Gly
65                  70                  75                  80

Leu Tyr Gly Glu Asn Leu Ala Trp Ser Gly Gly Ala Leu Ser Gly Ala
                85                  90                  95

Glu Ala Val Lys Leu Trp Val Asn Glu Lys Ser Asp Tyr Ile Tyr Ala
            100                 105                 110

Ser Asn Thr Cys Ser Asp Gly Lys Gln Cys Gly His Tyr Thr Gln Val
        115                 120                 125

Val Trp Arg Thr Ser Glu Trp Val Gly Cys Ala Lys Val Lys Cys Asp
    130                 135                 140

Asn Gly Gly Thr Phe Val Thr Cys Asn Tyr Tyr Pro Pro Gly Asn Tyr
145                 150                 155                 160

Arg Gly Arg Trp Pro Tyr
                165
```

```
<210> SEQ ID NO 3
<211> LENGTH: 226
<212> TYPE: PRT
<213> ORGANISM: Arabidopsis thaliana

<400> SEQUENCE: 3

Met Asn Thr Phe Lys Thr Pro Phe Leu Ile Ile Val Ala Ile Ser Phe
1               5                   10                  15

Leu Val Leu Ala Thr Asn Ala Gln Asn Ala Gln Gln Asp Tyr Leu Asn
            20                  25                  30

Thr His Asn Thr Ala Arg Ala Gln Val Gly Val Ala Asn Val Val Trp
        35                  40                  45

Asp Thr Val Val Ala Ala Tyr Ala Thr Asn Tyr Ala Asn Ala Arg Lys
    50                  55                  60

Val Asp Cys Ser Leu Thr Pro Ser Thr Gly Gly Ser Tyr Gly Glu Asn
65                  70                  75                  80

Leu Ala Asn Gly Asn Asn Ala Leu Phe Thr Gly Val Ala Ala Val Asn
                85                  90                  95

Leu Trp Val Asn Glu Lys Pro Tyr Tyr Asn Tyr Thr Ala Asn Ala Cys
            100                 105                 110

Ile Gly Ala Gln Gln Cys Lys His Tyr Thr Gln Val Val Trp Ser Asn
        115                 120                 125

Ser Val Lys Ile Gly Cys Ala Arg Val Leu Cys Asn Asn Gly Gly Tyr
    130                 135                 140

Phe Val Gly Cys Asn Tyr Asp Ala Ser Ala Ala Leu Lys Ser Arg Lys
145                 150                 155                 160

Ile Thr Ala Ser Val Arg Gln Thr Arg Gly Leu Gly Ala Ser Ala Ala
                165                 170                 175

Cys Gly Gln Leu Arg Asn Lys Phe Gln Lys Ser Pro Ser Leu Ala Thr
            180                 185                 190

Ala Glu Gly Glu Val Ile Glu Ala Arg Leu Arg Ser Glu Asp Phe Asp
        195                 200                 205

Asn Ser Cys Ile Gly Phe Ala Phe Thr Tyr Ile Cys Asp Ala Cys Val
    210                 215                 220

Gly Leu
225


<210> SEQ ID NO 4
<211> LENGTH: 205
<212> TYPE: PRT
<213> ORGANISM: Arabidopsis thaliana

<400> SEQUENCE: 4

Met Ser Ser Ser Ser Leu Tyr His Pro Phe Cys Leu Ser Ile Ser Ser
1               5                   10                  15

Val Leu Leu Leu Leu Leu Leu Ile Phe Ser Gly Glu Phe Pro Ser Thr
            20                  25                  30

Ala Gly Thr Ser Ser Pro Asp Thr Lys Ala Ala Ala Ala Arg Ala Thr
        35                  40                  45

Asn Arg Gly Arg Arg Asn Lys Gln Ser Ala Glu Phe Leu Leu Ala His
    50                  55                  60

Asn Ala Ala Arg Val Ala Ser Gly Ala Ser Asn Leu Arg Trp Asp Gln
65                  70                  75                  80

Gly Leu Ala Arg Phe Ala Ser Lys Trp Ala Lys Gln Arg Lys Ser Asp
                85                  90                  95
```

```
Cys Lys Met Thr His Ser Gly Gly Pro Tyr Gly Glu Asn Ile Phe Arg
            100                 105                 110

Tyr Gln Arg Ser Glu Asn Trp Ser Pro Arg Arg Val Val Asp Lys Trp
        115                 120                 125

Met Asp Glu Ser Leu Asn Tyr Asp Arg Val Ala Asn Thr Cys Lys Ser
    130                 135                 140

Gly Ala Met Cys Gly His Tyr Thr Gln Ile Val Trp Arg Thr Thr Thr
145                 150                 155                 160

Ala Val Gly Cys Ala Arg Ser Lys Cys Asp Asn Asn Arg Gly Phe Leu
                165                 170                 175

Val Ile Cys Glu Tyr Ser Pro Ser Gly Asn Tyr Glu Gly Glu Ser Pro
            180                 185                 190

Phe Asp Ile Pro Lys Ile Thr Leu Lys Leu Asp Lys Ile
        195                 200                 205


<210> SEQ ID NO 5
<211> LENGTH: 241
<212> TYPE: PRT
<213> ORGANISM: Arabidopsis thaliana

<400> SEQUENCE: 5

Met Glu Leu Arg Lys Arg Lys Ile Arg Ala Pro Leu His Ile Phe Val
1               5                   10                  15

Gly Ile Thr Phe Phe Leu Leu Gln Leu Trp Ser Gly Thr Ala Gln Ile
            20                  25                  30

Asn His Glu Asp Ser Ser Thr Lys Pro Ser Val Lys Asn Ser Pro Ser
        35                  40                  45

Ala Thr Ser Thr Arg Leu Leu Leu Ser Pro Pro Ser Phe Thr Gly Asn
    50                  55                  60

Arg Phe Ser Phe Arg Phe Arg Trp Arg Arg Ile Arg Arg Arg Asn Arg
65                  70                  75                  80

Val Asn Arg Ala Ser Arg Glu Phe Leu Ile Ala His Asn Leu Val Arg
                85                  90                  95

Ala Arg Val Gly Glu Pro Pro Phe Gln Trp Asp Gly Arg Leu Ala Ala
            100                 105                 110

Tyr Ala Arg Thr Trp Ala Asn Gln Arg Val Gly Asp Cys Arg Leu Val
        115                 120                 125

His Ser Asn Gly Pro Tyr Gly Glu Asn Ile Phe Trp Ala Gly Lys Asn
    130                 135                 140

Asn Trp Ser Pro Arg Asp Ile Val Asn Val Trp Ala Asp Glu Asp Lys
145                 150                 155                 160

Phe Tyr Asp Val Lys Gly Asn Thr Cys Glu Pro Gln His Met Cys Gly
                165                 170                 175

His Tyr Thr Gln Ile Val Trp Arg Asp Ser Thr Lys Val Gly Cys Ala
            180                 185                 190

Ser Val Asp Cys Ser Asn Gly Gly Val Tyr Ala Ile Cys Val Tyr Asn
        195                 200                 205

Pro Pro Gly Asn Tyr Glu Gly Glu Asn Pro Phe Gly Ser Tyr Asp Asp
    210                 215                 220

Gln Ile Gly Leu Ala Arg Asp Asp Pro Pro Ala Val Ile Gly Gly Met
225                 230                 235                 240

Ala


<210> SEQ ID NO 6
```

```
<211> LENGTH: 207
<212> TYPE: PRT
<213> ORGANISM: Arabidopsis thaliana

<400> SEQUENCE: 6

Met Ala Thr Thr Ser Ser Thr Lys Gln Val Ile Val Phe Thr Ile Ser
1               5                   10                  15

Leu Leu Leu Val Ala Phe Gln Ala Val His Ala Asp Tyr Tyr Arg Gln
            20                  25                  30

Arg Pro Pro Val Thr Pro Thr Pro Tyr Val Pro Lys Pro Arg Tyr Pro
        35                  40                  45

Leu Pro Ser Pro Ser Pro Lys Pro Val Tyr Arg Pro Pro Thr Thr Pro
    50                  55                  60

Ser Leu Pro Ala Gly Ser Ile Ala Arg Leu Phe Leu Asp Pro His Asn
65                  70                  75                  80

Ala Leu Arg Ser Gly Leu Gly Leu Pro Pro Leu Ile Trp Asp Gly Lys
                85                  90                  95

Leu Ala Ser Tyr Ala Thr Trp Trp Ala Asn Gln Arg Arg Tyr Asp Cys
            100                 105                 110

Ser Leu Thr His Ser Thr Gly Pro Tyr Gly Glu Asn Leu Phe Trp Gly
        115                 120                 125

Ser Gly Ser Ser Trp Ala Pro Gly Phe Ala Val Gln Ser Trp Ile Val
    130                 135                 140

Glu Gly Arg Ser Tyr Asn His Asn Thr Asn Ser Cys Asp Gly Ser Gly
145                 150                 155                 160

Met Cys Gly His Tyr Thr Gln Met Val Trp Arg Asp Thr Lys Arg Leu
                165                 170                 175

Gly Cys Ala Arg Val Val Cys Glu Asn Gly Ala Gly Val Phe Ile Thr
            180                 185                 190

Cys Asn Tyr Asp Pro Pro Gly Asn Tyr Val Gly Glu Lys Pro Tyr
        195                 200                 205


<210> SEQ ID NO 7
<211> LENGTH: 210
<212> TYPE: PRT
<213> ORGANISM: Arabidopsis thaliana

<400> SEQUENCE: 7

Met Ala Thr Thr Thr Ser Thr Gln Ala Ile Val Phe Ala Ile Ala Leu
1               5                   10                  15

Phe Leu Val Ala Ile Gln Ala Val His Ala Asp Tyr Tyr Arg His Arg
            20                  25                  30

Pro Gln Arg Pro Ile Thr Pro Ser Pro Pro Pro Tyr Val Ala Lys Pro
        35                  40                  45

Gln Pro Leu Pro Thr Pro Ser Pro Lys Pro Ile Leu Tyr Gln Pro Pro
    50                  55                  60

Pro Thr Tyr Gln Pro Pro Thr Gly Ser Phe Glu Gln Gln Phe Leu Asp
65                  70                  75                  80

Pro His Asn Thr Val Arg Gly Gly Leu Gly Leu Pro Pro Leu Val Trp
                85                  90                  95

Asp Val Lys Ile Ala Ser Tyr Ala Thr Trp Trp Ala Asn Gln Arg Arg
            100                 105                 110

Tyr Asp Cys Ser Leu Thr His Ser Thr Gly Pro Tyr Gly Glu Asn Leu
        115                 120                 125

Phe Trp Gly Ser Gly Ser Asp Phe Thr Ser Thr Phe Ala Val Glu Ser
    130                 135                 140
```

```
Trp Thr Val Glu Ala Lys Ser Tyr Asn His Met Thr Asn Thr Cys Glu
145                 150                 155                 160

Gly Asp Gly Met Cys Gly His Tyr Thr Gln Ile Val Trp Arg Glu Thr
                165                 170                 175

Arg Arg Leu Gly Cys Ala Arg Val Val Cys Glu Asn Gly Ala Gly Val
            180                 185                 190

Phe Ile Thr Cys Asn Tyr Asp Pro Pro Gly Asn Tyr Val Gly Glu Lys
        195                 200                 205

Pro Tyr
    210


<210> SEQ ID NO 8
<211> LENGTH: 190
<212> TYPE: PRT
<213> ORGANISM: Arabidopsis thaliana

<400> SEQUENCE: 8

Met Ser Ser Ser Tyr Leu Arg Val Ile Leu Leu Leu Gly Ala Leu Asn
1               5                   10                  15

Val Val Val Ser Leu Ser Ile Thr Asn Ser Leu Ile Thr Lys Ser Ala
            20                  25                  30

Thr Leu Gly Gln Val Phe Arg Ile Cys Lys Asn Leu Cys Pro Gly Cys
        35                  40                  45

Asp His Asp Ser Leu Gln Phe Leu Phe Arg His Asn Leu Val Arg Ala
    50                  55                  60

Ala Arg Phe Glu Pro Pro Leu Ile Trp Asp Arg Arg Leu Gln Asn Tyr
65                  70                  75                  80

Ala Gln Gly Trp Ala Asn Gln Arg Arg Gly Asp Cys Ala Leu Arg His
                85                  90                  95

Ser Val Ser Asn Gly Glu Phe Asn Leu Gly Glu Asn Ile Tyr Trp Gly
            100                 105                 110

Tyr Gly Ala Asn Trp Ser Pro Ala Asp Ala Val Val Ala Trp Ala Ser
        115                 120                 125

Glu Lys Arg Phe Tyr His Tyr Gly Ser Asn Thr Cys Asp Ala Gly Gln
    130                 135                 140

Met Cys Gly His Tyr Thr Gln Ile Val Trp Lys Ser Thr Arg Arg Val
145                 150                 155                 160

Gly Cys Ala Arg Val Val Cys Asp Asn Gly Gly Ile Phe Met Thr Cys
                165                 170                 175

Asn Tyr Asp Pro Pro Gly Asn Tyr Ile Gly Gln Lys Pro Tyr
            180                 185                 190


<210> SEQ ID NO 9
<211> LENGTH: 186
<212> TYPE: PRT
<213> ORGANISM: Arabidopsis thaliana

<400> SEQUENCE: 9

Met Ser Val Thr Leu Ser His Pro Ser Ser Cys Leu Leu Leu Leu Phe
1               5                   10                  15

Leu Leu Phe Ser Gly His Pro Ser Val Leu Gly Thr Ser Ile Pro Asp
            20                  25                  30

Ala Val Asn Thr Ala Ala Arg Leu Val Asn Arg Ala Arg Arg Ala Lys
        35                  40                  45

Leu Ser Arg Glu Phe Leu Gln Ala His Asn Asp Ala Arg Val Ser Ser
    50                  55                  60
```

```
Gly Val Pro Thr Leu Gly Trp Asp Arg Asp Leu Ala Arg Phe Ala Asp
65                  70                  75                  80

Lys Trp Ala Lys Gln Arg Lys Ser Asp Cys Ser Met Ile His Ser Gly
                85                  90                  95

Gly Pro Tyr Gly Glu Asn Ile Phe Trp His Arg Arg Lys Lys Thr Trp
            100                 105                 110

Ser Pro Glu Lys Val Val Thr Arg Trp Phe Glu Glu Arg Phe Asn Tyr
        115                 120                 125

Asp Val Lys Thr Asn Thr Cys Ala Pro Gly Lys Met Cys Gly His Tyr
    130                 135                 140

Thr Gln Met Val Trp Arg Glu Thr Thr Ala Val Gly Cys Ala Arg Val
145                 150                 155                 160

Lys Cys His Asn Gly Arg Gly Tyr Leu Val Val Cys Glu Tyr Asp Pro
                165                 170                 175

Arg Gly Asn Tyr Glu Gly Glu Arg Pro Phe
            180                 185


<210> SEQ ID NO 10
<211> LENGTH: 185
<212> TYPE: PRT
<213> ORGANISM: Arabidopsis thaliana

<400> SEQUENCE: 10

Met Glu Gln Lys Thr Leu Ile Phe Ile Ile Ile Ile Ile Val Ile Ser
1               5                   10                  15

Thr Pro Leu Pro Ser Leu Ser Phe Gln Ile Pro Ser Asn Arg Thr Pro
            20                  25                  30

Thr Thr Ser Thr Leu Ile Phe Ser Gln Asp Lys Ala Leu Ala Arg Asn
        35                  40                  45

Thr Ile Gln Gln Gln Phe Leu Arg Pro His Asn Ile Leu Arg Ala Lys
    50                  55                  60

Leu Arg Leu Pro Pro Leu Lys Trp Ser Asn Ser Leu Ala Leu Tyr Ala
65                  70                  75                  80

Ser Arg Trp Ala Arg Thr Arg Arg Gly Asp Cys Lys Leu Ile His Ser
                85                  90                  95

Gly Gly Pro Tyr Gly Glu Asn Leu Phe Trp Gly Ser Gly Lys Gly Trp
            100                 105                 110

Thr Pro Arg Asp Ala Val Ala Ala Trp Ala Ser Glu Met Lys Tyr Tyr
        115                 120                 125

Asp Arg Arg Thr Ser His Cys Lys Ala Asn Gly Asp Cys Leu His Tyr
    130                 135                 140

Thr Gln Leu Val Trp Lys Lys Ser Ser Arg Ile Gly Cys Ala Ile Ser
145                 150                 155                 160

Phe Cys Lys Thr Gly Asp Thr Phe Ile Ile Cys Asn Tyr Asp Pro Pro
                165                 170                 175

Gly Asn Ile Val Gly Gln Pro Pro Phe
            180                 185


<210> SEQ ID NO 11
<211> LENGTH: 185
<212> TYPE: PRT
<213> ORGANISM: Arabidopsis thaliana

<400> SEQUENCE: 11

Met Ala Leu Thr His His Ile Ile Phe Val Ala Leu Leu Val Ile Ser
1               5                   10                  15
```

```
Val Lys Ala Ile Ser Pro Ala Ala Lys Leu Lys Pro Lys Gln Ile Val
            20                  25                  30

Ser Thr Ser Pro Pro Pro Pro Pro Thr Ile Ser Ala Ala Ala Lys Ala
        35                  40                  45

Phe Thr Asp Ala His Asn Lys Ala Arg Ala Met Val Gly Val Pro Pro
    50                  55                  60

Leu Val Trp Ser Gln Thr Leu Glu Ala Ala Ala Ser Arg Leu Ala Arg
65                  70                  75                  80

Tyr Gln Arg Asn Gln Lys Lys Cys Glu Phe Ala Ser Leu Asn Pro Gly
                85                  90                  95

Lys Tyr Gly Ala Asn Gln Leu Trp Ala Lys Gly Leu Val Ala Val Thr
            100                 105                 110

Pro Ser Leu Ala Val Glu Thr Trp Val Lys Glu Lys Pro Phe Tyr Asn
        115                 120                 125

Tyr Lys Ser Asp Thr Cys Ala Ala Asn His Thr Cys Gly Val Tyr Lys
    130                 135                 140

Gln Val Val Trp Arg Asn Ser Lys Glu Leu Gly Cys Ala Gln Ala Thr
145                 150                 155                 160

Cys Thr Lys Glu Ser Thr Val Leu Thr Ile Cys Phe Tyr Asn Pro Pro
                165                 170                 175

Gly Asn Val Ile Gly Gln Lys Pro Tyr
            180                 185


<210> SEQ ID NO 12
<211> LENGTH: 161
<212> TYPE: PRT
<213> ORGANISM: Arabidopsis thaliana

<400> SEQUENCE: 12

Met Ala Phe Pro Ser Cys Val Ser Val Ala Ile Thr Ala Met Met Leu
1               5                   10                  15

Leu Val Thr Cys Cys His Cys Ala Thr Tyr Gln Glu Gln Phe Met Gly
            20                  25                  30

Pro Gln Asn Ala Ala Arg Ala His Leu Arg Leu Lys Pro Leu Lys Trp
        35                  40                  45

Asp Ala Lys Leu Ala Arg Tyr Ala Gln Trp Trp Ala Asn Gln Arg Arg
    50                  55                  60

Gly Asp Cys Ala Leu Thr His Ser Asn Gly Pro Tyr Gly Glu Asn Leu
65                  70                  75                  80

Phe Trp Gly Ser Gly Asn Arg Trp Gly Pro Ser Gln Ala Ala Tyr Gly
                85                  90                  95

Trp Leu Ser Glu Ala Arg Ser Tyr Asn Tyr Arg Ser Asn Ser Cys Asn
            100                 105                 110

Ser Glu Met Cys Gly His Tyr Thr Gln Ile Val Trp Lys Asn Thr Gln
        115                 120                 125

Lys Ile Gly Cys Ala His Val Ile Cys Asn Gly Gly Gly Gly Val Phe
    130                 135                 140

Leu Thr Cys Asn Tyr Asp Pro Pro Gly Asn Phe Leu Gly Arg Lys Pro
145                 150                 155                 160

Tyr


<210> SEQ ID NO 13
<211> LENGTH: 161
<212> TYPE: PRT
<213> ORGANISM: Arabidopsis thaliana
```

<400> SEQUENCE: 13

```
Met Asn Thr Phe Lys Thr Pro Phe Leu Val Ile Val Ala Ile Ser Phe
1               5                   10                  15

Leu Val Val Ala Thr Asn Ala Gln Asn Thr Pro Gln Asp Tyr Leu Asn
            20                  25                  30

Ser His Asn Thr Ala Arg Ala Gln Val Gly Val Pro Asn Val Val Trp
        35                  40                  45

Asp Thr Thr Leu Ala Ala Tyr Ala Leu Asn Tyr Ser Asn Phe Arg Lys
    50                  55                  60

Ala Asp Cys Asn Leu Val His Ser Asn Gly Pro Tyr Gly Glu Asn Leu
65                  70                  75                  80

Ala Lys Gly Ser Ser Ser Ser Phe Ser Ala Ile Ser Ala Val Lys Leu
                85                  90                  95

Trp Val Asp Glu Lys Pro Tyr Tyr Ser Tyr Ala Tyr Asn Asn Cys Thr
            100                 105                 110

Gly Gly Lys Gln Cys Leu His Tyr Thr Gln Val Val Trp Arg Asp Ser
        115                 120                 125

Val Lys Ile Gly Cys Ala Arg Val Gln Cys Thr Asn Thr Trp Trp Phe
    130                 135                 140

Val Ser Cys Asn Tyr Asn Ser Pro Gly Asn Trp Val Gly Glu Tyr Pro
145                 150                 155                 160

Tyr
```

<210> SEQ ID NO 14
<211> LENGTH: 161
<212> TYPE: PRT
<213> ORGANISM: Arabidopsis thaliana

<400> SEQUENCE: 14

```
Met Ser Leu Leu Lys Thr Asn Ile Leu Phe Leu Leu Ala Ile Ala Leu
1               5                   10                  15

Phe Tyr Gly Ser Leu Ala Glu Asp Leu Gln Gln Gln Phe Leu Glu Ala
            20                  25                  30

His Asn Glu Ala Arg Asn Glu Val Gly Leu Asp Pro Leu Val Trp Asp
        35                  40                  45

Asp Glu Val Ala Ala Tyr Ala Ala Ser Tyr Ala Asn Gln Arg Ile Asn
    50                  55                  60

Asp Cys Ala Leu Val His Ser Asn Gly Pro Phe Gly Glu Asn Ile Ala
65                  70                  75                  80

Met Ser Ser Gly Glu Met Ser Ala Glu Asp Ala Ala Glu Met Trp Ile
                85                  90                  95

Asn Glu Lys Gln Tyr Tyr Asp Tyr Asp Ser Asn Thr Cys Asn Asp Pro
            100                 105                 110

Asn Gly Gly Thr Cys Leu His Tyr Thr Gln Val Val Trp Lys Asn Thr
        115                 120                 125

Val Arg Leu Gly Cys Ala Lys Val Val Cys Asn Ser Gly Gly Thr Phe
    130                 135                 140

Ile Thr Cys Asn Tyr Asp Pro Pro Gly Asn Tyr Ile Gly Glu Lys Pro
145                 150                 155                 160

Phe
```

<210> SEQ ID NO 15
<211> LENGTH: 163
<212> TYPE: PRT

```
<213> ORGANISM: Arabidopsis thaliana

<400> SEQUENCE: 15

Met Lys Ile Phe Asn Ser Ser Gln Asn Leu Phe Leu Ala Ile Thr Phe
1               5                   10                  15

Phe Leu Val Leu Ile Val His Leu Lys Ala Gln Asp Ser Pro Gln Asp
            20                  25                  30

Phe Leu Ala Val His Asn Arg Ala Arg Ala Glu Val Gly Val Gly Pro
        35                  40                  45

Leu Arg Trp Asp Glu Lys Val Ala Ala Tyr Ala Arg Asn Tyr Ala Asn
    50                  55                  60

Gln Arg Lys Gly Asp Cys Ala Met Lys His Ser Ser Gly Ser Tyr Gly
65                  70                  75                  80

Glu Asn Ile Ala Trp Ser Ser Gly Ser Met Thr Gly Val Ala Ala Val
                85                  90                  95

Asp Met Trp Val Asp Glu Gln Phe Asp Tyr Asp Tyr Asp Ser Asn Thr
            100                 105                 110

Cys Ala Trp Asp Lys Gln Cys Gly His Tyr Thr Gln Val Val Trp Arg
        115                 120                 125

Asn Ser Glu Arg Leu Gly Cys Ala Lys Val Arg Cys Asn Asn Gly Gln
    130                 135                 140

Thr Phe Ile Thr Cys Asn Tyr Asp Pro Pro Gly Asn Trp Val Gly Glu
145                 150                 155                 160

Trp Pro Tyr


<210> SEQ ID NO 16
<211> LENGTH: 166
<212> TYPE: PRT
<213> ORGANISM: Arabidopsis thaliana

<400> SEQUENCE: 16

Met Lys Met Phe Ile Ser Pro Gln Thr Leu Val Leu Leu Ala Leu Ala
1               5                   10                  15

Leu Val Leu Ala Phe Ala Val Pro Leu Lys Ala Gln Asp Arg Arg Gln
            20                  25                  30

Asp Tyr Leu Asp Val His Asn His Ala Arg Asp Asp Val Ser Val Pro
        35                  40                  45

His Ile Lys Trp His Ala Gly Ala Ala Arg Tyr Ala Trp Asn Tyr Ala
    50                  55                  60

Gln Arg Arg Lys Arg Asp Cys Arg Leu Ile His Ser Asn Ser Arg Gly
65                  70                  75                  80

Arg Tyr Gly Glu Asn Leu Ala Trp Ser Ser Gly Asp Met Ser Gly Ala
                85                  90                  95

Ala Ala Val Arg Leu Trp Val Arg Glu Lys Ser Asp Tyr Phe His Lys
            100                 105                 110

Ser Asn Thr Cys Arg Ala Gly Lys Gln Cys Gly His Tyr Thr Gln Val
        115                 120                 125

Val Trp Lys Asn Ser Glu Trp Val Gly Cys Ala Lys Val Lys Cys Asp
    130                 135                 140

Asn Gly Gly Thr Phe Val Thr Cys Asn Tyr Ser His Pro Gly Asn Val
145                 150                 155                 160

Arg Gly Arg Arg Pro Tyr
                165


<210> SEQ ID NO 17
```

<211> LENGTH: 160
<212> TYPE: PRT
<213> ORGANISM: Arabidopsis thaliana

<400> SEQUENCE: 17

```
Met Phe Asn Ser Tyr Pro Asn Leu Leu Val Leu Ala Ile Ala Leu Ala
1               5                   10                  15

Leu Ser Phe Ser Val Pro Leu Lys Ala Gln Asp Gln Pro Gln Asp Tyr
            20                  25                  30

Phe Asn Ala His Asn Arg Ala Arg Val Ser Val Gly Val Ser Pro Leu
        35                  40                  45

Met Trp Ser Gln Thr Leu Thr Ala Tyr Ala Gln Ala Tyr Ala Glu Lys
    50                  55                  60

Arg Arg Asp Cys Gly Leu Phe Leu Ser Gly Gly Pro Tyr Gly Glu Thr
65                  70                  75                  80

Ile Lys Ala Asp Ile Ile Asp Phe Ser Ala Glu Glu Phe Val Ser Thr
                85                  90                  95

Phe Leu Asn Gln Lys Ser Asp Tyr Asp Tyr Thr Thr Asn Thr Cys Arg
            100                 105                 110

Ala Gly Lys Ser Cys Asp Gly Tyr Lys Gln Val Leu Phe Arg Lys Ser
        115                 120                 125

Val Phe Leu Gly Cys Ala Lys Val Lys Cys Asn Asn Gly Gly Phe Leu
    130                 135                 140

Ala Ile Cys Ser Tyr Asp Pro Ser Val Ile Leu Ser Glu Arg Pro Phe
145                 150                 155                 160
```

<210> SEQ ID NO 18
<211> LENGTH: 177
<212> TYPE: PRT
<213> ORGANISM: Arabidopsis thaliana

<400> SEQUENCE: 18

```
Met Ser Ser Phe Arg Tyr Thr Phe Val Leu Leu Thr Leu Leu Ser Val
1               5                   10                  15

Leu Leu Thr Arg Ala Tyr Gly Leu Pro Arg Val Arg Pro Ile Lys Asp
            20                  25                  30

Val Gln Pro Arg Lys Thr Leu Lys Val His Asn Gln Ile Arg Ala Ala
        35                  40                  45

Val Gly Val Ala Pro Leu Lys Trp Asn Lys Thr Val Ala Ala Tyr Ala
    50                  55                  60

Gln Lys Phe Ala Asn Arg Gln Ala Lys Ala Gly Val Cys Asp Tyr Ser
65                  70                  75                  80

Ser Met Arg His Ser Asp Gly Pro Tyr Gly Glu Asn Ile Ala Ala Gly
                85                  90                  95

Trp Val Gln Pro Lys Asp Gln Met Ser Gly Pro Ile Ala Ala Lys Tyr
            100                 105                 110

Trp Leu Thr Glu Lys Pro Asn Tyr Asp His Ala Thr Asn Lys Cys Lys
        115                 120                 125

Asp Val Cys Gly His Tyr Thr Gln Met Val Ala Asn Gln Ser Leu Ser
    130                 135                 140

Leu Gly Cys Gly Ser Phe Arg Cys His Glu Asn Glu Leu Ile Tyr Ile
145                 150                 155                 160

Val Cys Asn Tyr Tyr Pro Met Pro Val Gly Asp Glu Asn Thr Arg Pro
                165                 170                 175

Tyr
```

<210> SEQ ID NO 19
<211> LENGTH: 172
<212> TYPE: PRT
<213> ORGANISM: Arabidopsis thaliana

<400> SEQUENCE: 19

```
Met Phe His Lys Val Ala Ile Glu Thr Leu Val Leu Leu Leu Leu Ile
1               5                   10                  15

Asn Tyr Leu Thr Gln Ile Asp Val Ser Ser Ala Gln Tyr Ser Gln Tyr
            20                  25                  30

Pro Gln Ser His Glu Tyr Pro Asp Ser Tyr Leu Arg Pro His Asn Ala
        35                  40                  45

Ala Arg Ala Ala Val Lys Val Lys Pro Leu Arg Trp Asp Phe Gly Ile
    50                  55                  60

Ala Thr Val Ala Gln Asp Tyr Ala Asn His Leu Ala Ser Gly Pro Cys
65                  70                  75                  80

Ser Leu Glu His Ser Ser Gly Pro Tyr Gly Glu Asn Leu Ala Phe Gly
                85                  90                  95

Ser Gly Asp Met Ser Ala Ala Gln Ala Val Ala Met Trp Val His Glu
            100                 105                 110

Lys Ser Tyr Tyr Asp Phe Tyr Ser Asn Ser Cys His Gly Pro Ala Cys
        115                 120                 125

Gly His Tyr Thr Gln Val Val Trp Arg Gly Ser Ala Arg Leu Gly Cys
    130                 135                 140

Gly Lys Ala Lys Cys Asn Asn Gly Ala Ser Ile Val Val Cys Asn Tyr
145                 150                 155                 160

Asp Pro Ala Gly Asn Tyr Ile Gly Ala Arg Pro Tyr
                165                 170
```

<210> SEQ ID NO 20
<211> LENGTH: 165
<212> TYPE: PRT
<213> ORGANISM: Arabidopsis thaliana

<400> SEQUENCE: 20

```
Met Ser Phe Ser Gly Tyr Ser Phe Ile Val Leu Thr Leu Leu Ser Ile
1               5                   10                  15

Val Leu Thr Gln Ile Tyr Gly Leu Arg Ser Phe Ser Arg Met Asp Asp
            20                  25                  30

Leu Gln Pro Ala Glu Thr Leu Ala Val His Asn Gln Ile Arg Ala Ala
        35                  40                  45

Asp Gln Lys Leu Ala Ala His Ala Gln Arg Tyr Ala Asn Val Arg Ser
    50                  55                  60

Gln Asp Cys Ala Met Lys Tyr Ser Thr Asp Gly Thr Tyr Gly Glu Asn
65                  70                  75                  80

Ile Ala Ala Gly Trp Val Gln Pro Met Asp Thr Met Ser Gly Pro Ile
                85                  90                  95

Ala Thr Lys Phe Trp Phe Thr Glu Lys Pro Tyr Tyr Asn Tyr Ala Thr
            100                 105                 110

Asn Lys Cys Ser Glu Pro Cys Gly His Tyr Thr Gln Ile Val Ala Asn
        115                 120                 125

Gln Ser Thr His Leu Gly Cys Gly Thr Val Arg Cys Phe Lys Asn Glu
    130                 135                 140

Tyr Val Trp Val Val Cys Asn Tyr Ala Pro Arg Pro Met Gly Asp Ala
145                 150                 155                 160
```

-continued

```
Asn Thr Arg Pro Tyr
                165


<210> SEQ ID NO 21
<211> LENGTH: 6
<212> TYPE: PRT
<213> ORGANISM: Artificial Sequence
<220> FEATURE:
<223> OTHER INFORMATION: consensus sequence of CAP

<400> SEQUENCE: 21

Phe Thr Gln Ile Val Trp
1               5
```

PEPTIDE HAVING PLANT STEM CELL-INDUCING EFFECT AND PLANT PEST RESISTANCE-INDUCING EFFECT

CROSS-REFERENCE TO RELATED APPLICATIONS

This application is a U.S. National Stage application of PCT/JP2021/034176 filed 16 Sep. 2021, which claims priority to Japanese application No. 2020-156361 filed 17 Sep. 2020, the entire disclosures of which are hereby incorporated by reference in their entireties.

SEQUENCE LISTING

The present application contains a Sequence Listing which has been submitted electronically in ASCII format and is hereby incorporated by reference in its entirety. Said ASCII copy, created on 2 Mar. 2023, is named 0223_0106-PCT-US_Sequence_Listing.txt and is 32 kilobytes in size.

TECHNICAL FIELD

The present invention relates to a peptide, a plant stem cell inducer, an environmental stress enhancer, a plant pest resistance inducer, a germination promoter, a transformation efficiency enhancer, and a plant growth promoter. The present invention also relates to a method for producing plant stem cells, a method for enhancing the environmental stress tolerance of a plant body, a plant pest control method, a method for promoting plant seed germination, a method for transforming a plant, and a method for promoting the growth of a plant body.

BACKGROUND OF THE INVENTION

Methods to promote stem cell transformation in plants include methods using plant hormones. A mass of undifferentiated cells produced by such a method is called a "callus." However, only a few plants can increase such callus tissues, and there is a severe problem that it takes several weeks to generate callus tissues.

In the previous studies in angiosperms, such as *Arabidopsis thaliana*, it has been possible to produce meristematic tissues containing stem cells by creating genetically modified plants by transformation of specific genes, such as the KNOX family. However, since only some of differentiated cells that repeat cell division can be transformed into stem cells, it is difficult to identify cells having an ability to become stem cells, and the mechanism that transforms differentiated cells into stem cells is not well understood. In addition, this approach cannot be applied to plants that are difficult to transform, and there is a problem that it is difficult to use genetically modified plants obtained by transformation outside the laboratory.

It has been possible to generate freezing-tolerant and drought-tolerant plants, and pest-resistant plants by transforming and controlling specific genes, such as transcription factors related to freezing tolerance and drought tolerance, and transcription factors related to disease resistance. However, such an approach cannot be applied to plants that are difficult to transform, and there is also a problem that it is difficult to use genetically modified plants obtained by transformation outside the laboratory.

There are also conventional methods to protect plants from pests by using pesticides. However, the use of pesticides has a concern of disadvantages, such as health effects, negative environmental impact, and increasing pests harboring pesticide resistance.

It has been possible to promote germination by treating seeds with a plant hormone, gibberellin. However, in general, the germination rate of plant seeds harvested more than 3 years before is significantly reduced, and almost no germination occurs after 5 years or more.

In addition, it has been possible to improve transformation efficiency by introducing a plasmid that expresses GABA aminotransferase gene, which has a function to suppress GABA generation, into *Agrobacterium*. However, even when a plasmid that expresses GABA aminotransferase gene is used, the efficiency is increased up to only about 3-fold.

PTL 1 and PTL 2 have reported other methods to promote stem cell transformation in plants.

PTL 1 discloses a method for producing dedifferentiation cells, comprising a dedifferentiation induction step of subjecting all or a part of a plant body to heat shock treatment at 28° C. to 42° C. for 30 minutes to 5 days, and a culturing step of culturing the plant body after the dedifferentiation induction step at an ordinary growth temperature for the plant.

Further, PTL 2 discloses a method for producing a plant body, comprising producing, in a plant body, a chimeric protein that fuses a transcription factor promoting the transcription of a gene for inhibiting dedifferentiation or redifferentiation with a functional peptide for transforming any transcription factor to a transcription-inhibiting factor, thereby promoting the dedifferentiation or redifferentiation of the plant body.

CITATION LIST

Patent Literature

PTL 1: JP2015-208256A
PTL 2: JP2012-187040A

SUMMARY OF INVENTION

Technical Problems to be Solved by the Present Invention

An object of the present invention is to provide a peptide having a plant stem cell-inducing effect, a plant environmental stress tolerance-enhancing effect, a plant pest resistance-inducing effect, a germination-promoting effect, a plant transformation efficiency-enhancing effect, and a plant growth-promoting effect, as well as a plant stem cell inducer, an environmental stress enhancer, a plant pest resistance inducer, a germination promoter, a transformation efficiency enhancer, and a plant growth promoter, all of which comprise the peptide. Another object of the present invention is to provide a method for producing plant stem cells, a method for enhancing the environmental stress tolerance of a plant body, a plant pest control method, a method for promoting plant seed germination, a method for transforming a plant body, and a method for promoting the growth of a plant body, all of which use the above peptide.

Solution to Solve the Problems

As a result of intensive studies to achieve the above objects, the present inventors found that differentiated cells can be transformed into stem cells only by immersing plants in a solution containing a synthetic peptide consisting of the conserved region of cysteine-rich secretory protein, antigen 5, and pathogenesis-related 1 (CAP) for a short period of time. The inventors also found that plants with enhanced freezing tolerance, drought tolerance, and pest resistance can be produced by immersing plants in a solution containing the peptide, or by applying a solution containing the peptide to plants. In addition, the inventors found that germination can be promoted by immersing plant seeds in a solution containing the peptide, transformation efficiency can be enhanced by performing plant transformation in the presence of the peptide, and the growth of plants can be promoted by applying a solution containing the peptide to the plants.

The present invention has been completed by conducting further studies based on these findings. The present invention provides the following peptide, plant stem cell inducer, environmental stress enhancer, plant pest resistance inducer, method for producing plant stem cells, method for enhancing the environmental stress tolerance of a plant body, plant pest control method, and the like.

Item 1. A peptide that is a partial peptide of cysteine-rich secretory protein, antigen 5, and pathogenesis-related 1 (CAP), consisting of an amino acid sequence of the conserved region of CAP, the peptide having at least one effect selected from the following effects: a plant stem cell-inducing effect, a plant environmental stress tolerance-enhancing effect, a plant pest resistance-inducing effect, a germination-promoting effect, a plant transformation efficiency-enhancing effect, and a plant growth-promoting effect.

Item 2. The peptide according to Item 1, wherein CAP is secreted from a gall-inducing insect.

Item 3. A peptide comprising an amino acid sequence represented by formula (I):

$$(X^1)_n TQX^2X^3W \quad (I)$$

wherein $X^1$ represents phenylalanine or tyrosine, $X^2$ represents isoleucine or valine, $X^3$ represents isoleucine or valine, and n represents 0 or 1;

and having 25 or less amino acid residues.

Item 4. The peptide according to any one of Items 1 to 3, which is a peptide consisting of all or a part of an amino acid sequence represented by SEQ ID NO: 1.

Item 5. A plant stem cell inducer comprising the peptide according to any one of Items 1 to 4.

Item 6. A plant environmental stress tolerance enhancer comprising the peptide according to any one of Items 1 to 4.

Item 7. The environmental stress tolerance enhancer according to Item 6, wherein the environmental stress tolerance is drought tolerance, osmotic tolerance, salt tolerance, or freezing tolerance.

Item 8. A plant pest resistance inducer comprising the peptide according to any one of Items 1 to 4.

Item 9. A germination promoter comprising the peptide according to any one of Items 1 to 4.

Item 10. A plant transformation efficiency enhancer comprising the peptide according to any one of Items 1 to 4.

Item 11. A plant growth promoter comprising the peptide according to any one of Items 1 to 4.

Item 12. A method for producing plant stem cells, comprising applying the peptide according to any one of Items 1 to 4 to a plant body.

Item 13. A method for enhancing the environmental stress tolerance of a plant body, comprising applying the peptide according to any one of Items 1 to 4 to the plant body.

Item 14. A plant pest control method comprising applying the peptide according to any one of Items 1 to 4 to a plant body.

Item 15. A method for promoting plant seed germination, comprising applying the peptide according to any one of Items 1 to 4 to plant seeds.

Item 16. A method for transforming a plant body, comprising transforming the plant body in the presence of the peptide according to any one of Items 1 to 4.

Item 17. A method for promoting the growth of a plant body, comprising applying the peptide according to any one of Items 1 to 4 to the plant body.

Advantageous Effects of the Invention

Since the peptide of the present invention has an excellent plant stem cell-inducing effect, plant environmental stress tolerance (e.g., drought tolerance, osmotic tolerance, or freezing tolerance)-enhancing effect, plant pest resistance-inducing effect, germination-promoting effect, plant transformation efficiency-enhancing effect, and plant growth-promoting effect, exposing plants to the peptide of the present invention can transform differentiated cells of the plants into stem cells, enhance the environmental stress tolerance (e.g., drought tolerance, osmotic tolerance, or freezing tolerance) of the plants, enhance the pest resistance of the plants, promote the germination of plant seeds, enhance plant transformation efficiency, and promote the growth of the plant bodies.

Since most species of animals and plants have the CAP gene in common, most plants also have receptors for CAP. Therefore, the peptide of the present invention is expected to be able to, for various plants, induce stem cell transformation, enhance environmental stress tolerance, enhance pest resistance, promote germination, enhance transformation efficiency, and promote growth.

Stem cell transformation requires only short-term exposure of plants to the peptide of the present invention, and is extremely simple and fast-acting. Further, since all cells infiltrated with the peptide of the present invention are transformed into stem cells, it is easy to identify cells that have differentiated into stem cells.

The peptide of the present invention does not require the process of transformation, and thus can basically be applied to any plants, and can be used both inside and outside the laboratory. Further, the peptide of the present invention is not toxic to living organisms unlike pesticides, and is decomposed by microorganisms in the environment, which causes no problem with residue.

The peptide of the present invention makes it possible to germinate seeds harvested more than 8 years before or not germinated by gibberellin treatment. Further, the peptide of the present invention not only significantly enhances transformation efficiency, but also allows transformation of plants that have not been able to transform thus far. In addition, the peptide of the present invention has an effect of promoting the growth of plants, which makes it possible to economically increase the production of crops without excessive fertilization.

BRIEF DESCRIPTION OF DRAWINGS

FIG. 1 shows the alignment of the CAP protein sequences of *Arabidopsis thaliana* (At), *Schlechtendalia chinensis* (Sc), *Borboryctis euryae* (Be), *Caloptilia cecidophora* (Cc), and *Caloptilia ryukyuensis* (Cr).

FIG. 2 shows the results obtained in Test Example 1. *Arabidopsis thaliana* expressing stem cell marker PLT1-GFP was immersed in water (A, C) or 600 nM of the peptide aqueous solution (B, D) for 2 days. (A, B) are GFP fluorescent images, and (C, D) are bright field images.

DESCRIPTION OF EMBODIMENTS

Figure 3:
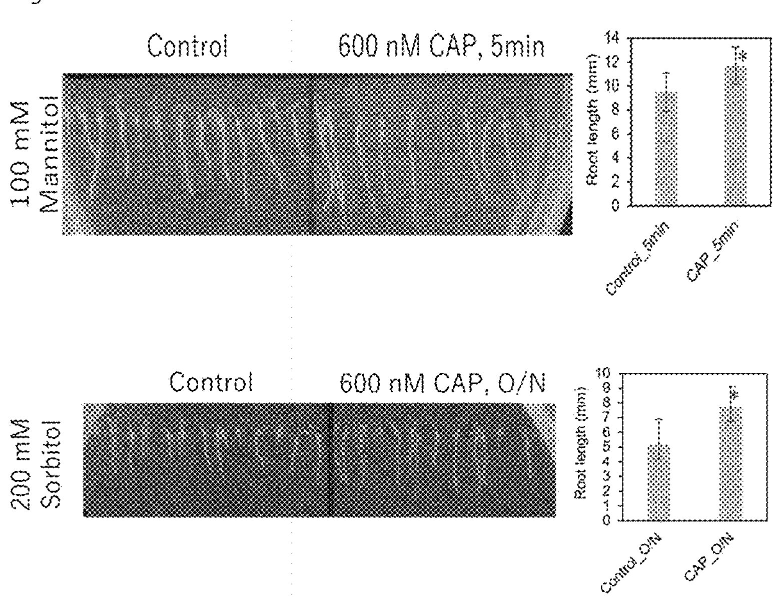
FIG. 3 shows the effect of imparting osmotic tolerance and drought tolerance by treatment with the peptide of the present invention. The upper figure shows the growth on an excess mannitol-containing medium after immersion in 600 nM CAP peptide for 5 minutes. The values in the graphs are mean values 9.50 (S.D.=1.61) and 11.69 (S.D.=1.55), and *p<0.05 (Student's t-test). The lower figure shows the growth on an excess sorbitol-containing medium after immersion in 600 nM CAP peptide overnight. The values in the graphs are mean values 5.17 (S.D.=1.73) and 7.71 (S.D.=1.39), and *p<0.05 (Student's t-test).

Embodiments of the present invention are described below.

In the present specification, the term "comprise" includes the meanings of "essentially consisting of" and "consisting of."

In the present specification, the gene encoding CAP is referred to as "CAP gene," and the simple expression "CAP" means the protein. In the present specification, amino acids are expressed in one-letter notation, unless otherwise specified.

The peptide of the present invention, in an embodiment, is a partial peptide of cysteine-rich secretory protein, antigen 5, and pathogenesis-related 1 (CAP), consisting of an amino acid sequence of the conserved region of CAP, and having at least one of a plant stem cell-inducing effect, a plant environmental stress tolerance-enhancing effect, a plant pest resistance-inducing effect, a germination-promoting effect, a plant transformation efficiency-enhancing effect, and a plant growth-promoting effect (hereinafter also referred to as "peptide 1 of the present invention").

CAP (cysteine-rich secretory protein, antigen 5, and pathogenesis-related 1) belongs to the CAP superfamily. Most species of animals and plants have CAP in common, and some species of animals and plants may have many CAP proteins. Amino acid sequences of CAP are registered on the NCBI website as, for example, Ref Seq Accession No. NP_197985 (SEQ ID NO: 2), NP_175427 (SEQ ID NO: 3), NP_195893 (SEQ ID NO: 4), NP_171638 (SEQ ID NO: 5), NP_680450 (SEQ ID NO: 6), NP_194309 (SEQ ID NO: 7), NP_194308 (SEQ ID NO: 8), NP_187570 (SEQ ID NO: 9), NP_194875 (SEQ ID NO: 10), NP_201460 (SEQ ID NO: 11), NP_194761 (SEQ ID NO: 12), NP_175428 (SEQ ID NO: 13), NP_188603 (SEQ ID NO: 14), NP 195098 (SEQ ID NO: 15), NP 195097 (SEQ ID NO: 16), NP 192524 (SEQ ID NO: 17), NP_179587 (SEQ ID NO: 18), NP_195099 (SEQ ID NO: 19), and NP_179588 (SEQ ID NO: 20) (all *Arabidopsis thaliana*).

Further, the unknown amino acid sequences of CAP other than those registered on the database as described above can be obtained by known methods. As such a method, for example, RNA is extracted from organisms, RNA-Seq analysis is performed, and transcripts annotated as CAP are obtained as the amino acid sequences of CAP peptides.

CAP of the present invention widely includes CAP having a naturally occurring amino acid sequence, and variants obtained by substitution, addition, deletion, and/or insertion of one or two or more amino acids in the amino acid sequence of this CAP, and having biological activities equivalent to those of proteins consisting of the above amino acid sequence.

The range of "one or two or more" is not particularly limited, and means, for example, 1 to 50, preferably 1 to 25, more preferably 1 to 12, even more preferably 1 to 9, and particularly preferably 1 to 5. Techniques of substitution, addition, deletion, and/or insertion of one or two or more amino acids in specific amino acid sequences are known.

Peptide 1 of the present invention is a part of the amino acid sequence of CAP, and consists of an amino acid sequence of the conserved region. The conserved region of CAP is generally located near the C-terminal and can be determined by multiple alignment of CAP derived from various organisms.

Multiple alignment can be performed using analysis tools available on the market or via telecommunication lines (Internet). The number of amino acid residues in the conserved region of CAP is not particularly limited, and is, for example, 6 to 10, 6 to 11, 6 to 12, 6 to 13, 6 to 14, 6 to 15, 6 to 16, 6 to 17, 6 to 18, 6 to 19, 6 to 20, 6 to 21, 6 to 22, 6 to 23, 6 to 24, or 6 to 25.

CAP may be derived from any of microorganisms, animals, and plants. Among these, CAP produced by insects is preferred, and CAP secreted by gall-inducing insects is more preferred. Examples of gall-inducing insects include, but are not particularly limited to, *Schlechtendalia chinensis, Borboryctis euryae, Caloptilia cecidophora, Caloptilia ryukyuensis*, and the like.

In the present invention, the "plant stem cell-inducing effect" refers to the effect of transforming plant differentiated cells into stem cells (dedifferentiation) or the effect of maintaining stem cells (undifferentiated cells) without differentiation. Plant stem cells refer to plant cells having pluripotency and cell division ability, and include a callus.

In the present invention, the "plant environmental stress tolerance-enhancing effect" refers to the effect of rendering plants substantially immune to undesired effects of environmental stress or the effect of reducing the effects. The environmental stress as mentioned herein is not particularly limited, and examples include salt stress, drought stress, osmotic stress, temperature (e.g., high temperature, low temperature, or freezing) stress, and the like. The plant environmental stress tolerances in the present invention are preferably drought tolerance, osmotic tolerance, salt tolerance, and freezing tolerance.

In the present invention, the "plant pest resistance-inducing effect" refers to the effect of inducing the resistance of plants to pathogens and pests. Induction of pest resistance also includes enhancement of pest resistance.

In the present invention, the "transformation efficiency-enhancing effect" refers to the effect of enhancing the ratio of transformed plants, and also means that plants that have been unable, or almost unable, to transform can be transformed. The method of transformation is preferably an Agrobacterium method.

In the present invention, the "plant growth-promoting effect" includes expansion and hypertrophy of stems, expansion and hypertrophy of roots, growth of leaves, promotion of branching, increase in the fruiting rate, growth of fruit, and the like.

Peptide 1 of the present invention has at least one of a plant stem cell-inducing effect, a plant environmental stress tolerance-enhancing effect, a plant pest resistance-inducing effect, a germination-promoting effect, a plant transformation efficiency-enhancing effect, and a plant growth-promoting effect; preferably at least 2, 3, 4 or 5 of them; and more preferably all of them.

The peptide of the present invention, in another embodiment, comprises an amino acid sequence represented by formula (I):

$$(X^1)_n TQX^2X^3W \quad \text{(I)}$$

wherein $X^1$ represents phenylalanine or tyrosine, $X^2$ represents isoleucine or valine, $X^3$ represents isoleucine or valine, and n represents 0 or 1;

and has 25 or less amino acid residues (hereinafter also referred to as "peptide 2 of the present invention").

In peptide 2 of the present invention, n is preferably 1, and $X^1$ is preferably phenylalanine. As shown in the Examples provided later, in CAP secreted by gall-inducing insects, $X^1$ is phenylalanine. Further, $X^2$ is preferably isoleucine, and $X^3$ is preferably valine.

The number of amino acid residues in peptide 2 of the present invention is, for example, 25 or less, 24 or less, 23 or less, 22 or less, 21 or less, 20 or less, 19 or less, 18 or less, 17 or less, 16 or less, 15 or less, 14 or less, 13 or less, 12 or less, 11 or less, or 10 or less.

In peptide 2 of the present invention, the part other than the amino acid sequence represented by formula (I) is composed of any amino acids. Any amino acids used herein are not particularly limited as long as the effects of the present invention (plant stem cell-inducing effect, plant environmental stress tolerance-enhancing effect, plant pest resistance-inducing effect, germination-promoting effect, plant transformation efficiency-enhancing effect, and plant growth-promoting effect) are obtained. It is particularly desirable to use the amino acids at the corresponding positions of CAP derived from various organisms.

Examples of peptides 1 and 2 of the present invention (hereinafter simply referred to as "the peptide of the present invention") include peptides consisting of all or a part of the amino acid sequence represented by SEQ ID NO: 1 (TQVVWKSTTNIGVGILIVNGTV). The peptide consisting of a part of the amino acid sequence represented by SEQ ID NO: 1 is preferably one containing at least 5 residues from the N-terminal of SEQ ID NO: 1. The number of amino acid residues in the peptide consisting of a part of the amino acid sequence represented by SEQ ID NO: 1 is not particularly limited, and is, for example, 5 to 10, 5 to 11, 5 to 12, 5 to 13, 5 to 14, 5 to 15, 5 to 16, 5 to 17, 5 to 18, 5 to 19, 5 to 20, or 5 to 21.

Examples of the peptide of the present invention also include peptides consisting of an amino acid sequence having deletion, substitution, insertion, and/or addition of 1 to 10, 1 to 5, 1 to 4, 1 to 3, 1 to 2, or 1 amino acid in the amino acid sequence represented by SEQ ID NO: 1, and having at least one of a plant stem cell-inducing effect, a plant environmental stress tolerance-enhancing effect, a plant pest resistance-inducing effect, a germination-promoting effect, a plant transformation efficiency-enhancing effect, and a plant growth-promoting effect. In the case of amino acid substitution, it is considered that the activity of the original polypeptide is likely to be maintained if the amino acid is substituted with an amino acid of similar properties. Techniques of deletion, substitution, insertion, and/or addition of one or two or more amino acids in specific amino acid sequences are known.

The peptide of the present invention also includes salts thereof. Examples of the "salts" include sodium salts, potassium salts, calcium salts, hydrochlorides, sulfates, nitrates, magnesium salts, ammonium salts, phosphates, and organic acid salts (acetate, trifluoroacetate, citrate, maleate, oxalate, malate, lactate, succinate, propionate, fumarate, formate, picrate, benzoate, benzenesulfonate, etc.) of the peptide.

The peptide of the present invention also includes derivatives thereof. The term "derivatives" as used herein refers to those obtained by modifying the functional groups of the peptide of the present invention by modification, addition, mutation, substitution, deletion, or the like by known methods. Examples include those obtained by modifying the N-terminal, C-terminal, or amino acid side chain of the peptide of the present invention with a protecting group or the like. Examples of derivatives include those undergoing acetylation, palmitoylation, amidation, myristylation, dansylation, acrylation, biotinylation, phosphorylation, anilidation, succinylation, benzyloxycarbonylation, formylation, nitration, sulfonation, aldehydration, glycosylation, cyclization, monomethylation, dimethylation, trimethylation, guanidinylation, maleylation, trifluoroacetylation, trinitrophenylation, carbamylation, polyethylene glycolation, acetoacetylation, labeling (e.g., with fluorescent dyes), and the like.

The amino acids that constitute the peptide of the present invention may be L-form or D-form. Further, the amino acids that constitute the polypeptide of the present invention are not limited to natural amino acids, and may be non-natural amino acids.

The peptide of the present invention can be produced by using a known synthesis method such as solid-phase synthesis or liquid-phase synthesis, or by culturing a transformant introduced with a gene encoding the peptide. Examples of the host for producing the transformant include *E. coli*, yeast, mammalian cells, plant cells, insect cells, and the like.

The produced peptide can be purified by affinity chromatography, ion exchange chromatography, hydroxyapatite column chromatography, ammonium sulfate salting-out, or the like.

The plant stem cell inducer, plant environmental stress tolerance (e.g., drought tolerance, osmotic tolerance, salt tolerance, and freezing tolerance) enhancer, plant pest resistance inducer, germination promoter, plant transformation efficiency enhancer, and plant growth promoter of the present invention (hereinafter also collectively referred to as "the agent of the present invention") comprise the above peptide.

The method for producing plant stem cells, method for enhancing the environmental stress tolerance (e.g., drought tolerance, osmotic tolerance, salt tolerance, and freezing tolerance) of a plant body, plant pest control method, and method for promoting the growth of a plant body of the present invention each comprise applying the above peptide to the plant body. The method for promoting plant seed germination of the present invention comprises applying the above peptide to plant seeds. The method for transforming a plant body of the present invention comprises transforming the plant body in the presence of the above peptide.

The peptide of the present invention has an excellent plant stem cell-inducing effect, plant environmental stress tolerance (e.g., drought tolerance, osmotic tolerance, salt tolerance, or freezing tolerance)-enhancing effect, plant pest resistance-inducing effect, germination-promoting effect, plant transformation efficiency-enhancing effect, and plant growth-promoting effect. Therefore, the peptide of the present invention can be suitably used as an active ingredient of plant stem cell inducers, plant environmental stress tolerance enhancers, plant pest resistance inducers, germination promoters, plant transformation efficiency enhancers, and plant growth promoters.

Since most species of animals and plants have the CAP gene in common, most plants also have receptors for CAP. Therefore, the peptide of the present invention is expected to be able to, for various plants, induce stem cell transformation, enhance environmental stress tolerance, enhance pest resistance, promote germination, enhance transformation efficiency, and promote growth.

As components other than the peptide of the present invention, the agent of the present invention can suitably contain, if necessary, a support, surfactant, wetting agent, preservative, binder, stabilizer, coloring agent, emulsifier, dispersant, penetrant, thickener, antifoaming agent, and the like. Moreover, the agent of the present invention can be suitably formulated into a wettable powder, granule wettable powder, flowable agent, emulsion, dusting powder, dust formulation, aerosol, paste agent, suspension, solution, or the like by a known method. The agent of the present invention can be used as it is, or used after dilution with a diluent to a predetermined concentration. In addition to the peptide of the present invention, the plant pest resistance inducer of the present invention may further contain a pesticide, such as an insecticide or miticide.

The content of the peptide of the present invention in the plant stem cell inducer of the present invention is not particularly limited as long as the effects of the present invention are obtained, and is preferably 100 to 1000 nM, and more preferably 100 to 600 nM. The content of the peptide of the present invention in the environmental stress tolerance enhancer of the present invention is not particularly limited as long as the effects of the present invention are obtained, and is preferably 1 to 1000 nM, and more preferably 100 to 600 nM. The content of the peptide of the present invention in the plant pest resistance inducer of the present invention is not particularly limited as long as the effects of the present invention are obtained, and is preferably 1 to 600 nM, and more preferably 10 to 500 nM.

The content of the peptide of the present invention in the germination promoter of the present invention is not particularly limited as long as the effects of the present invention are obtained, and is preferably 0.1 to 1,000 μM, and more preferably 10 to 100 μM. The content of the peptide of the present invention in the transformation efficiency enhancer of the present invention is not particularly limited as long as the effects of the present invention are obtained, and is preferably 20 to 10,000 nM, and more preferably 50 to 1,000 nM. The content of the peptide of the present invention in the plant growth promoter of the present invention is not particularly limited as long as the effects of the present invention are obtained, and is preferably 0.1 to 5 μM, and more preferably 0.5 to 1 μM.

The method for applying the peptide of the present invention to a plant body is not particularly limited as long as the effects of the present invention are obtained. Examples include spraying (atomizing) to plant bodies, spraying on the soil surface, injection into the soil, blasting to plant seeds, smearing to plant seeds, immersion of plant seeds, and the like. The peptide of the present invention may be applied to all or a part of the plant body, and a part of the plant body includes leaves, bark, stems, trunks, fruits, seeds, flowers, roots, and the like. The peptide of the present invention may be applied to the plant body only once or repeatedly.

In the method for producing plant stem cells, it is preferable that the plant body is immersed in a solution containing the peptide of the present invention. Further, in the method for enhancing the environmental stress tolerance of a plant body, it is preferable that a solution containing the peptide of the present invention is sprayed (atomized) to the plant body, and that plant seeds are immersed in the solution. On the other hand, in the plant pest control method, it is preferable that a solution containing the peptide of the present invention is sprayed (atomized) to the plant body. In the method for promoting plant seed germination, it is preferable that plant seeds are immersed in a solution containing the peptide of the present invention. In the method for transforming a plant body, it is preferable that transformation is performed using an *Agrobacterium* solution containing the peptide of the present invention. On the other hand, in the method for promoting the growth of a plant body, it is preferable that a solution containing the peptide of the present invention is directly sprayed (atomized) to the plant body.

In the method for transforming a plant body of the present invention, the method of transformation is not particularly limited. In particular, it is preferable to perform transformation by an *Agrobacterium* method. The *Agrobacterium* method can be carried out by using a known means.

The time for immersing a plant body in a solution containing the peptide of the present invention is, for example, about 24 to 96 hours for inducing stem cell transformation, about 0.5 to 16 hours for enhancing drought tolerance, and about 1 to 10 minutes for enhancing osmotic tolerance. Further, the time for promoting plant seed germination is about 5 minutes to 5 hours.

The amounts of the plant stem cell inducer, environmental stress tolerance enhancer, germination promoter, transformation efficiency enhancer, and plant growth promoter of the present invention applied can be suitably selected depending on the target plant, dosage form, application method, etc. Further, the amount of the plant pest resistance inducer of the present invention applied can be suitably selected depending on the target pest, target pathogen, target harmful insect, target plant, dosage form, degree of pest occurrence, application method, etc.

Plants targeted by the agent of the present specification are not particularly limited, and may be angiosperms or gymnosperms. Angiosperms include both dicotyledonous and monocotyledonous plants. Examples of the targeted plants include the following: vegetables, such as leafy greens (e.g., Chinese cabbage, spinach, cabbage, lettuce, komatsuna, garland *chrysanthemum*, mizuna, welsh onion, onion, broccoli, and asparagus), root vegetables (e.g., carrot, radish, burdock, eddo, yam, lotus root, and turnip), and fruit vegetables (e.g., tomato, cherry tomato, eggplant, pepper, cucumber, watermelon, strawberry, pumpkin, melon, and sweet corn); fruit trees, such as apples, pears, grapes, and persimmons; legumes, such as soybeans, green beans, adzuki beans, fava beans, peanuts, and kidney beans; tea; tobacco; cotton; cereal grasses, such as barley, wheat, oat, and rye; flowering plants, such as pansies, marigolds, salvias, petunias, periwinkles, chrysanthemums, carnations, roses, gentians, baby's breath, gerberas, statice, prairie gentian, alstroemeria, lilies, tulips, cyclamens, *gladiolus*, freesias, primulas, dendrobiums, begonias, cymbidium, poinsettias, phalaenopsis, violas, daisies, *scoparia*, and calibrachoa; succulent plants, such as cacti; lawn grasses, such as cool-season grass and Korean lawn grass; and afforestation plants. Thus, the agent of the present invention can be widely used for agricultural crops, cultivars, research plants, and the like.

Plant diseases targeted by the plant pest resistance inducer of the present invention are not particularly limited as long as the effects of the present invention are obtained. Examples include the following plant diseases:

- blast (Pyricularia *oryzae*), sheath blight (*Thanatephorus cucumeris*), brown spot (*Cochliobolus miyabeanus*), bakanae disease (*Gibberella fujikuroi*), seedling blight (*Pythium* spp., *Fusarium* spp., *Trichoderma* spp., *Rhizopus* spp., *Rhizoctonia solani*, etc.), false smut (*Claviceps virens*), and kernel smut (Tilletia barclayana) of rice;
- powdery mildew (*Erysiphe graminis* f. sp. *hordei*), rust (*Puccinia striiformis, Puccinia graminis, Puccinia recondita, Puccinia hordei*), leaf stripe (*Pyrenophora graminea*), net blotch (*Pyrenophora teres*), *fusarium* head blight (*Fusarium graminearum, Fusarium culmorum, Fusarium avenaceum, Microdochium nivale*), typhula snow blight (Typhula *incarnata*, Typhula ishikariensis, Micronectriella *nivalis*), loose smut (*Ustilago nuda, Ustilago tritici, Ustilago nigra, Ustilago avenae*), bunt (Tilletia caries, Tilletia *pancicii*), eye spot (Pseudocercosporella herpotrichoides), foot-rot (*Rhizoctonia cerealis*), scald (Rhynchosporium secalis), leaf blotch (*Septoria tritici*), glume blotch (*Leptosphaeria nodorum*), seedling blight (*Fusarium* spp., *Pythium* spp., *Rhizoctonia* spp., *Septoria nodorum, Pyrenophora* spp.), take-all (Gaeumannomyces *graminis*), anthracnose (*Colletotrichum graminicola*), ergot (*Claviceps purpurea*), and spot blotch (*Cochliobolus sativus*) of wheat;
- *fusarium* head blight (*Fusarium graminearum*, etc.), seedling blight (*Fusarium avenaceum, Penicillium* spp., *Pythium* spp., *Rhizoctonia* spp.), rust (*Puccinia sorghi*), leaf blight (*Cochliobolus heterostrophus*), smut (*Ustilago maydis*), anthracnose (*Colletotrichum graminicola*), and northern leaf spot (*Cochliobolus carbonum*) of corn;
- gray mold (*Botrytis cinerea*) of tomato, cucumber, legumes, strawberry, potato, cabbage, eggplant, lettuce, etc.;
- stem rot (*Sclerotinia sclerotiorum*) of tomato, cucumber, legumes, strawberry, potato, rapeseed, cabbage, eggplant, lettuce, etc.;
- damping-off (*Rhizoctonia* spp., *Pythium* spp., *Fusarium* spp., *Phytophthora* spp., *Sclerotinia sclerotiorum*, etc.) of various vegetables, such as tomato, cucumber, legumes, radish, watermelon, eggplant, rapeseed, green pepper, spinach, and sugar beet;
- purple stain (*Cercospora kikuchii*), *sphaceloma* scab (*Elsinoe* glycines), pod and stem blight (*Diaporthe phaseolorum*), *Rhizoctonia* root rot (*Rhizoctonia solani*), root rot (*Phytophthora megasperma*), downy mildew (*Peronospora manshurica*), rust (*Phakopsora pachyrhizi*), and anthracnose (*Colletotrichum truncatum*) of soybean;
- downy mildew (*Pseudoperonospora cubensis*), powdery mildew (Sphaerotheca *fuliginea*), anthracnose (*Colletotrichum* lagenarium), gummy stem blight (*Mycosphaerella melonis*), *fusarium* wilt (*Fusarium oxysporum*), and *phytophthora* blight (*Phytophthora parasitica, Phytophthora melonis, Phytophthora nicotianae, Phytophthora drechsleri, Phytophthora capsici*, etc.) of gourds;
- leaf spot (*Alternaria brassicae*) of rapeseed;
- leaf spot (*Alternaria brassicae*, etc.), white spot (Cercosporella *brassicae*), blackleg (*Leptosphaeria maculans*), clubroot (Plasmodiophora *brassicae*), and downy mildew (*Peronospora brassicae*) of brassicaceae vegetables;
- bacterial leaf spot (*Pseudomonas syringae* pv tomato DC3000), early blight (*Alternaria solani*), leaf mold (*Cladosporium fulvum*), late blight (*Phytophthora infestans*), *fusarium* wilt (*Fusarium oxysporum*), root rot (*Pythium myriotylum, Pythium dissotocum*), and anthracnose (*Colletotrichum* phomoides) of tomato;
- damping-off (*Rhizoctonia solani*) and yellows (*Fusarium oxysporum*) of cabbage;
- bottom rot (*Rhizoctonia solani*) and yellows (*Verticillium dahliae*) of Chinese cabbage;
- rust (*Puccinia allii*), purple blotch (*Alternaria* porri), southern blight (*Sclerotium rolfsii*), and white tip disease (*Phytophthora* porri) of welsh onion;

powdery mildew (Sphaerotheca *fuliginea*, etc.), leaf mold (*Mycovellosiella* nattrassii), late blight (*Phytophthora infestans*), and brown rot (*Phytophthora capsici*) of eggplant;

leaf spot (*Mycosphaerella* personatum) and brown leaf spot (*Cercospora arachidicola*) of peanut;

powdery mildew (*Erysiphe pisi*), downy mildew (*Peronospora pisi*), and *mycosphaerella* blight (*Mycosphaerella pinodes*) of pea;

downy mildew (*Peronospora viciae*) and *phytophthora* rot (*Phytophthora nicotianae*) of broad bean;

anthracnose (*Colletotrichum lindemuthianum*) of kidney bean;

early blight (*Alternaria solani*), black scurf (*Rhizoctonia solani*), late blight (*Phytophthora infestans*), silver scurf (Spondylocladium *atrovirens*), dry rot (*Fusarium oxysporum, Fusarium solani*), and powdery scab (Spongospora *subterranea*) of potato;

powdery mildew (Sphaerotheca *humuli*), *phytophthora* rot (*Phytophthora nicotianae*), anthracnose (*Glomerella cingulata*), and fruit rot (*Pythium ultimum* Trow var. *ultimum*) of strawberry;

downy mildew (Plasmopara viticola), rust (*Phakopsora* ampelopsidis), powdery mildew (Uncinula necator), anthracnose (*Elsinoe ampelina*), ripe rot (*Glomerella cingulata*), black rot (*Guignardia* bidwellii), dead arm (*Phomopsis* viticola), flyspeck (Zygophiala *jamaicensis*), gray mold (*Botrytis cinerea*), bud blight (*Diaporthe* medusaea), violet root rot (Helicobasidium mompa), and white root rot (Rosellinia necatrix) of grape;

powdery mildew (*Podosphaera leucotricha*), scab (*Venturia inaequalis*), *alternaria* blotch (*Alternaria alternata* (apple pathotype)), rust (*Gymnosporangium* yamadae), blossom blight (Monilinia *mali*), canker (Valsa ceratosperma), ring rot (*Botryosphaeria* berengeriana), bitter rot (*Colletotrichum acutatum*), flyspeck (Zygophiala *jamaicensis*), sooty blotch (Gloeodes pomigena), fruit spot (*Mycosphaerella pomi*), violet root rot (Helicobasidium mompa), white root rot (Rosellinia necatrix), canker (*Phomopsis mali, Diaporthe* tanakae), and blotch (Diplocarpon *mali*) of apple;

anthracnose (Gloeosporium kaki), leaf spot (*Cercospora* kaki, *Mycosphaerella* nawae), and powdery mildew (Phyllactinia kakikora) of persimmon;

purple blotch (*Alternaria alternata* (Japanese pear pathotype)), scab (*Venturia* nashicola), rust (*Gymnosporangium* haraeanum), *physalospora* canker (*Physalospora* piricola), canker (*Diaporthe* medusaea, *Diaporthe* eres), and crown rot (*Phytophthora cactorum*) of pear;

melanose (*Diaporthe citri*), common green mold (*Penicillium digitatum*), blue mold (*Penicillium italicum*), and scab (*Elsinoe fawcettii*) of citrus;

stem rot (*Sclerotinia sclerotiorum*) of sunflower;

scab (*Cladosporium carpophilum*), *phomopsis* rot (*Phomopsis* sp.), *phytophthora* rot (*Phytophthora* sp.), and anthracnose (Gloeosporium laeticolor) of peach;

anthracnose (*Glomerella cingulata*), young-fruit rot (Monilinia kusanoi), and brown rot (Monilinia fructicola) of cherry;

black spot (Diplocarpon *rosae*), powdery mildew (Sphaerotheca *pannosa, Colletotrichum* gloesporioides), downy mildew (*Peronospora sparsa*), and *phytophthora* rot (*Phytophthora megasperma*) of rose;

brown spot (*Septoria chrysanthemi*-indici), rust (*Puccinia* horiana), and crown rot (*Phytophthora cactorum*) of *chrysanthemum*; and sooty mold of *Quercus* myrsinaefolia.

Plant pests targeted by the plant pest resistance inducer of the present invention are not particularly limited as long as the effects of the present invention are obtained. The plant pest resistance inducer of the present invention can be widely used for known pests, and is particularly suitable for agricultural pests.

Since the peptide of the present invention has an excellent plant stem cell-inducing effect, plant environmental stress tolerance-enhancing effect, and plant pest resistance-inducing effect, exposing plants to the peptide of the present invention can transform differentiated cells of the plants into stem cells, enhance the environmental stress tolerance of the plants, and enhance the pest resistance of the plants. Further, the peptide of the present invention has an excellent germination-promoting effect, plant transformation efficiency-enhancing effect, and plant growth-promoting effect, exposing plants to the peptide of the present invention can promote the germination of plant seeds, enhance plant transformation efficiency, and promote the growth of plant bodies. Therefore, it is an extremely simple method, and the peptide of the present invention has about 6 to 25 amino acid residues and is thus easy to synthesize.

The peptide of the present invention does not require the process of transformation, and thus can basically be applied to any plants, and can be used both inside and outside the laboratory.

Stem cell transformation requires only short-term exposure of plants to the peptide of the present invention, and is extremely simple and fast-acting. Further, since all cells infiltrated with the peptide of the present invention are transformed into stem cells, it is easy to identify cells that have differentiated into stem cells. Because it is possible to transform differentiated cells of various plants, including plants that are difficult to initialize and plants that are difficult to transform, into stem cells, the efficiency of tissue culture is considered to increase. Breed improvement in the state of callus becomes possible by performing stem cell transformation.

Moreover, the peptide of the present invention can enhance plant environmental stress tolerance, and makes it possible to protect crops from frost damage and cultivate crops in arid regions.

The peptide of the present invention can enhance the pest resistance of plants, and can protect crops from pests. Further, the peptide of the present invention is not toxic to living organisms unlike pesticides, and is decomposed by microorganisms in the environment, which causes no problem with residue. The peptide of the present invention can be applied to not only agricultural production sites, but also food crops, because it is not genetically modified and is safe.

The peptide of the present invention can promote the germination of plant seeds. It is possible not only to germinate old seeds, but also to revive plants thought to be extinct.

The peptide of the present invention can enhance plant transformation efficiency, allows transformation of plants that have not been able to transform, can develop research on plants that have not been able to be studied due to their inability to transform, and makes difficult-to-transform plants useful by genome editing or the like. In addition, the peptide of the present invention can promote the growth of plants, which makes it possible to economically increase the production of crops without excessive fertilization.

EXAMPLES

Examples are provided below to describe the present invention in more detail. However, the present invention is not limited to these Examples etc.

Test Example 1

The CAP protein sequences of *Arabidopsis thaliana, Schlechtendalia chinensis*, Borboryctis euryae, Caloptilia cecidophora, and Caloptilia ryukyuensis were aligned. As a result, FIG. 1 shows the conserved region conserved between the CAP proteins. The synthetic peptide in the boxed area in FIG. 1 (hereinafter referred to as "CAP peptide") was used in the following experiments.

*Arabidopsis thaliana* roots were treated with CAP peptide (TQVVWKSTTNIGVGILIVNGTV (SEQ ID NO: 1)). *Arabidopsis thaliana* expressing stem cell marker PLT1-GFP was immersed in water or a 600 nM peptide aqueous solution for 2 days, and GFP fluorescent images and bright field images were obtained with a confocal laser microscope.

The results are shown in FIG. 2. FIG. 2 indicates that the synthetic peptide from the conserved region of insect CAP induced a gall-like structure, and that differentiated cells were transformed into stem cells.

Test Example 2

RNA of *Arabidopsis thaliana* immersed in water or a 600 nM CAP peptide solution for 4 hours was extracted, and gene expression was compared by RNA-seq analysis. Network analysis was then performed on genes with increased expression.

The results showed that immersing the plant in 600 nM CAP peptide for 4 hours increased the expression of genes related to freezing tolerance and drought tolerance (by a factor of 2 or more).

Next, wild-type *Arabidopsis thaliana* seeds were immersed in water (Control) or 600 nM CAP peptide for 5 minutes and then grown on an excess mannitol-containing medium. Further, wild-type *Arabidopsis thaliana* seeds were immersed in water (Control) or 600 nM CAP peptide overnight, and then grown on an excess sorbitol-containing medium.

The results are shown in FIG. 3. In the excess mannitol-containing medium (high-osmotic pressure conditions), the plant roots treated with CAP peptide extended more (upper figure in FIG. 3), and in the excess sorbitol-containing medium (dry conditions), the plant roots treated with CAP peptide also extended more (lower figure in FIG. 3).

Test Example 3

RNA of *Arabidopsis thaliana* immersed in water or a 600 nM CAP peptide solution for 48 hours was extracted, and gene expression was compared by RNA-seq analysis. Network analysis was then performed.

The results showed that immersing the plant in 600 nM peptide for 48 hours increased the expression of genes related to disease resistance (by a factor of 2 to 3 or more).

Next, *Arabidopsis thaliana* leaves were sprayed with water/0.02% SILWET L-77 silicone surfactant (Control) or 600 nM CAP peptide/0.02% SILWET L-77 silicone surfactant, and 24 hours later, infected with *Pseudomonas syringae* pv tomato DC3000 (DC3000) with an OD600 of $0.2\times10^{-3}$. 2 days later, DC3000 obtained from leaf fragments cut into 4-mm -diameter circles was diluted and spotted on LB medium containing kanamycin. After incubation at 28° C. for 24 hours, the number of bacteria per unit area was counted.

Figure 4:
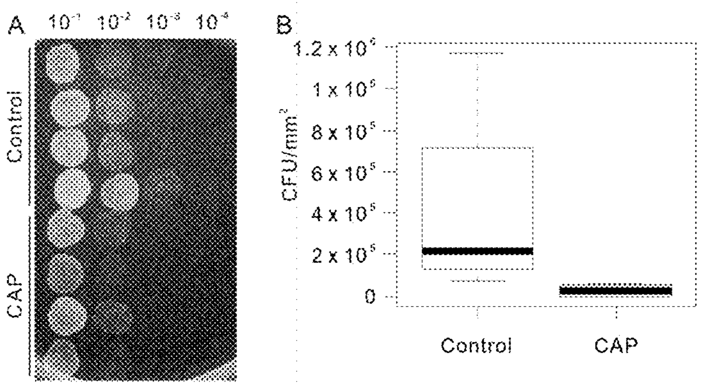
FIG. 4 shows the effect of inhibiting the growth of plant pathogen *Pseudomonas syringae* pv tomato DC3000 (DC3000) by spraying *Arabidopsis thaliana* leaves with water or a CAP peptide solution prior to the bacterial infection. Two days after infection, DC3000 obtained from leaf fragments (cut into 4-mm-diameter circles) was diluted, and then the diluted solutions were spotted on LB medium containing kanamycin, and incubated at 28° C. for 24 hours (A). Then, the number of bacteria per unit area was counted (B).

The results are shown in FIG. 4. Spraying *Arabidopsis thaliana* leaves with a 600 nM CAP peptide solution in advance suppressed the growth of bacteria after infection with plant pathogen *Pseudomonas syringae* pv tomato DC3000.

Test Example 4

*Arabidopsis thaliana* leaves applied with water or 60 nM CAP peptide were inoculated with *Pseudomonas syringae* DC3000.

Figure 5:
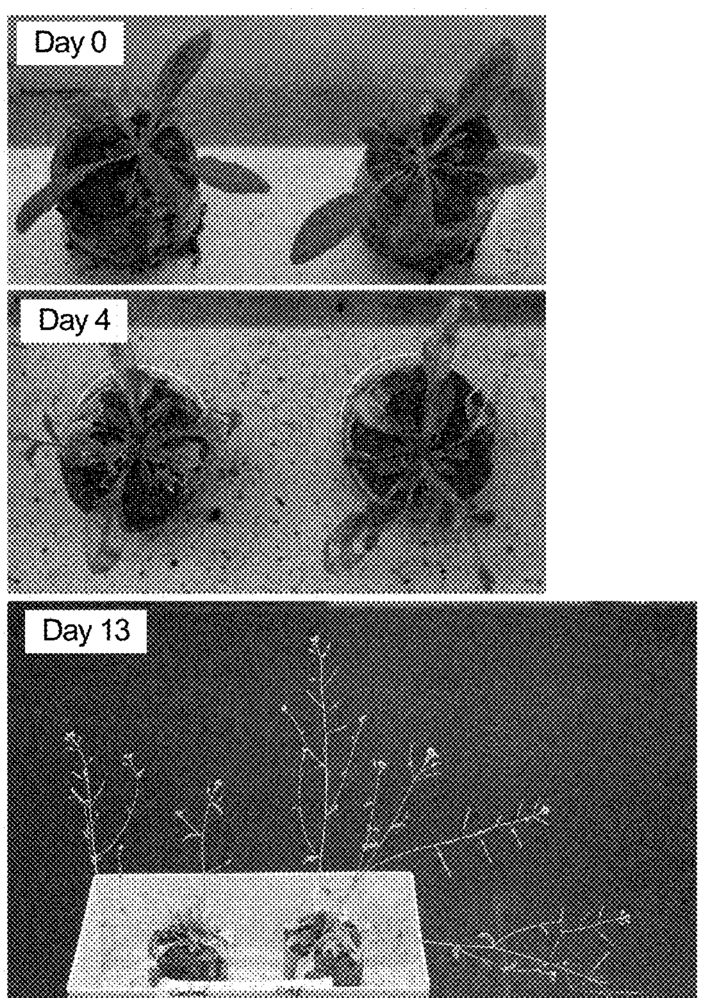
FIG. 5 shows the effect of inhibiting the growth of plant pathogen *Pseudomonas syringae* pv tomato DC3000 (DC3000) by spraying the peptide to *Arabidopsis thaliana* leaves with water (Control) or a 60 nM CAP peptide solution in advance. The photographs of both cases were taken at 0, 4, and 13 days after infection of water-treated or CAP peptide-treated *Arabidopsis thaliana* with plant pathogen DC3000.
Figure 6:
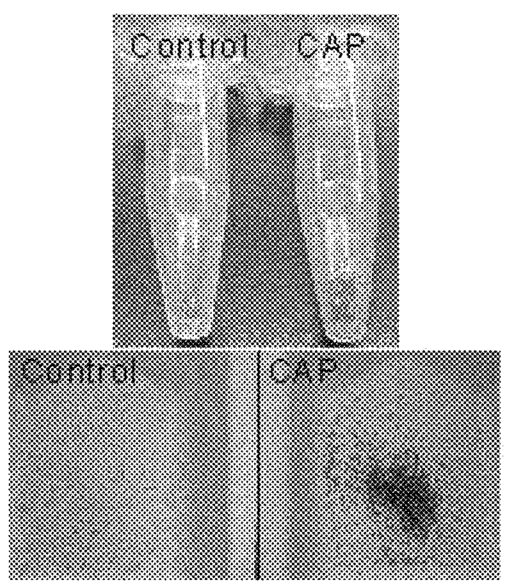
FIG. 6 shows the seeds collected from one individual of *Arabidopsis thaliana* of FIG. 5, showing the increase in the seed yield due to CAP peptide treatment.

The results are shown in FIGS. 5 and 6. 4 days later, the growth of the pathogen was significantly inhibited in the CAP peptide-treated plant body (middle figure in FIG. 5). At 13 days after infection, the CAP peptide-treated plant body grew much larger than the water treatment (Control) (lower figure in FIG. 5). At 13 days after pathogen infection, the CAP peptide-treated plant body grew much larger and yielded more seeds than the water treatment (Control) (FIG. 6).

Test Example 5

*Brassica rapa* leaves were sprayed with water or a 60 nM CAP peptide solution in advance, and one day later, inoculated with plant pathogen *Pseudomonas syringae* pv tomato DC3000 (DC3000). 2 days after infection, DC3000 obtained from leaf fragments cut into 4-mm-diameter circles was diluted, spotted on LB medium containing kanamycin, and incubated at 28° C. for 24 hours.

Figure 7:
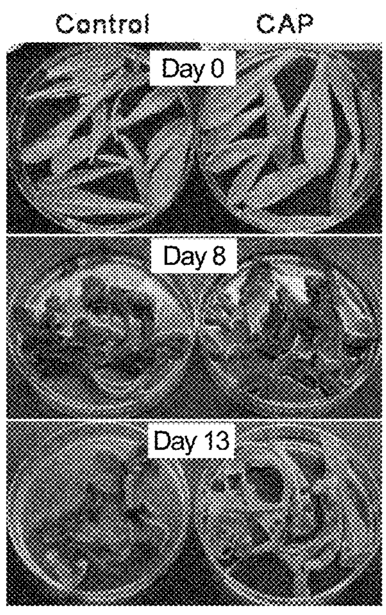
FIG. 7 shows photographs showing the effect of CAP peptide on infection of *Brassica rapa* with plant pathogen *Pseudomonas syringae* DC3000 (DC3000). *Brassica rapa* leaves were sprayed with water (Control) or a 60 nM CAP peptide solution in advance, and one day later, inoculated with plant pathogen DC3000. The photographs of both cases were taken at 0, 8, and 13 days after infection.
Figure 8:
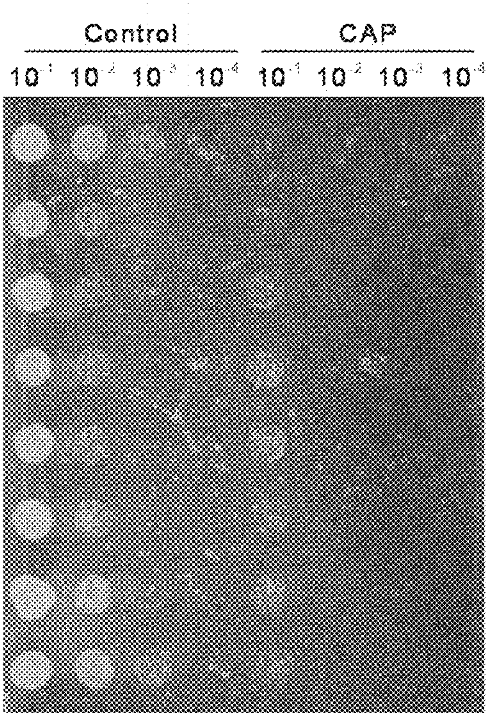
FIG. 8 shows photographs showing the effect of CAP peptide to inhibit the growth of the pathogen in *Brassica rapa*. *Brassica rapa* leaves were sprayed with water or a CAP peptide solution in advance, and one day later, inoculated with plant pathogen *Pseudomonas syringae* pv tomato DC3000 (DC3000). 2 days after infection, DC3000 obtained from leaf fragments cut into 4-mm-diameter circles was diluted, spotted on LB medium containing kanamycin, and incubated at 28° C. for 24 hours.

The results are shown in FIGS. 7 and 8. When the CAP peptide-treated *Brassica rapa* was treated with *Pseudomonas syringae* DC3000, the freshness was maintained for a longer period of time than the water treatment (Control) (FIG. 7). Further, 2 days after pathogen inoculation, the CAP peptide-treated *Brassica rapa* inhibited bacterial growth 1000 times or more, compared with the water treatment (Control) (FIG. 8).

Test Example 6

Figure 9:
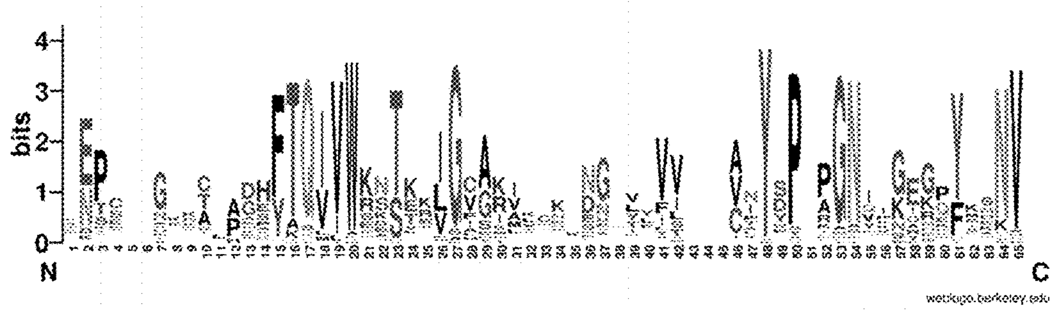
FIG. 9 shows the CAP consensus sequence of Schlechtendalia *chinensis*, Caloptilia cecidophora, Borboryctis euryae, Caloptilia ryukyuensis, *Rhus javanica*, and *Arabidopsis thaliana*.

Multiple types (76 types) of CAP proteins derived from *Schlechtendalia chinensis, Caloptilia cecidophora, Borboryctis euryae, Caloptilia ryukyuensis, Rhus javanica*, and *Arabidopsis thaliana* were aligned. From the consensus sequence (FIG. 9), FTQIVW (SEQ ID NO: 21) was determined (hereinafter referred to as "CAP6 peptide"). Then, *Arabidopsis thaliana* leaves were sprayed with 0.02% SILWET L-77 silicone surfactant (Control), 60 nM CAP peptide/0.02% SILWET L-77 silicone surfactant, or 60 nM CAP6 peptide/0.02% SILWET L-77 silicone surfactant, and 48 hours later, infected with *Pseudomonas syringae* pv tomato DC3000 (DC3000) with an OD600 of $0.2\times10^{-3}$. One day later, DC3000 obtained from leaf fragments cut into 5-mm-diameter circles was diluted and spotted on LB medium containing kanamycin. 24 hours later, the number of bacteria per unit area was counted.

Figure 10:
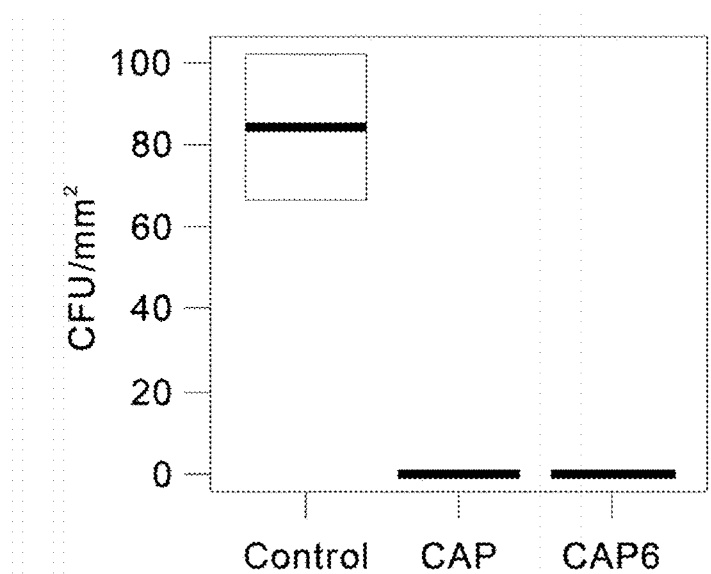
FIG. 10 is a graph showing the effect of CAP6 peptide on the infection with plant pathogen *Pseudomonas syringae* DC3000.

The results are shown in FIG. 10. When a disease tolerance test was performed using CAP6 peptide, a remarkable effect was obtained. Therefore, the peptide sequence showing the effect of the present invention is presumed to be F/Y-T-Q-I/V-V/I-W.

Test Example 7

*Arabidopsis thaliana* seeds harvested 10 years before and not naturally germinated were immersed in 0, 1, 10, or 100

μM CAP peptide for 2 hours and then sown. The germination rate was measured 2 weeks later.

Figure 11:
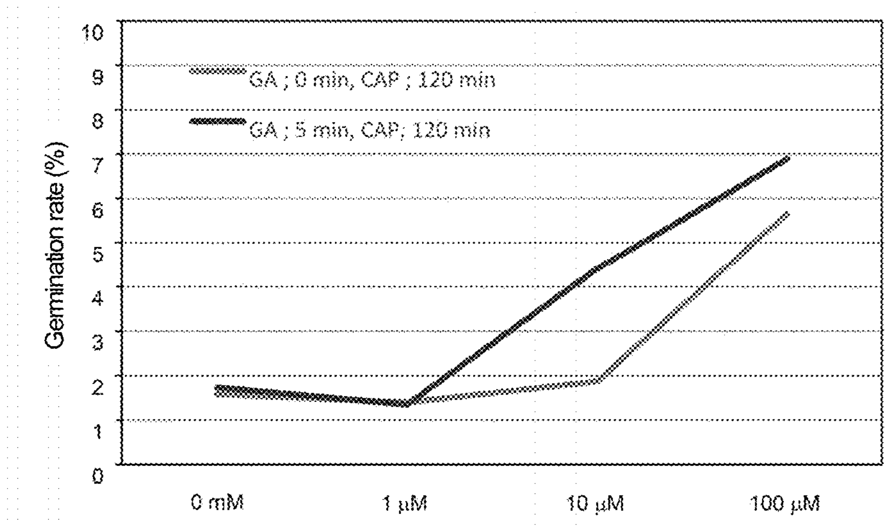
FIG. 11 is a graph showing the effect of promoting germination by treating *Arabidopsis thaliana* seeds with CAP peptide. The horizontal axis indicates the concentration of CAP peptide. n=126 (0 μM CAP, 0 mg/L GA), 143 (1 μM CAP, 0 mg/L GA), 107 (10 μM CAP, 0 mg/L GA), 53 (100 μM CAP, 0 mg/L GA), 115 (1 μM CAP, 0.1 mg/L GA), 74 (1 μM CAP, 0.1 mg/L GA), 68 (10 μM CAP, 0.1 mg/L GA), 58 (100 μM CAP, 0.1 mg/L GA)

The results are shown in FIG. 11. As a result, CAP peptide treatment of the *Arabidopsis thaliana* seeds resulted in a much higher germination rate than gibberellin treatment (FIG. 11).

Test Example 8

*Agrobacterium* introduced with a plasmid expressing GFP-TUB6 protein was mixed with CAP peptide to final concentrations of 50 nM, 1 μM, and 10 μM, and transformed into *Rorippa aquatica.*

Figure 12:
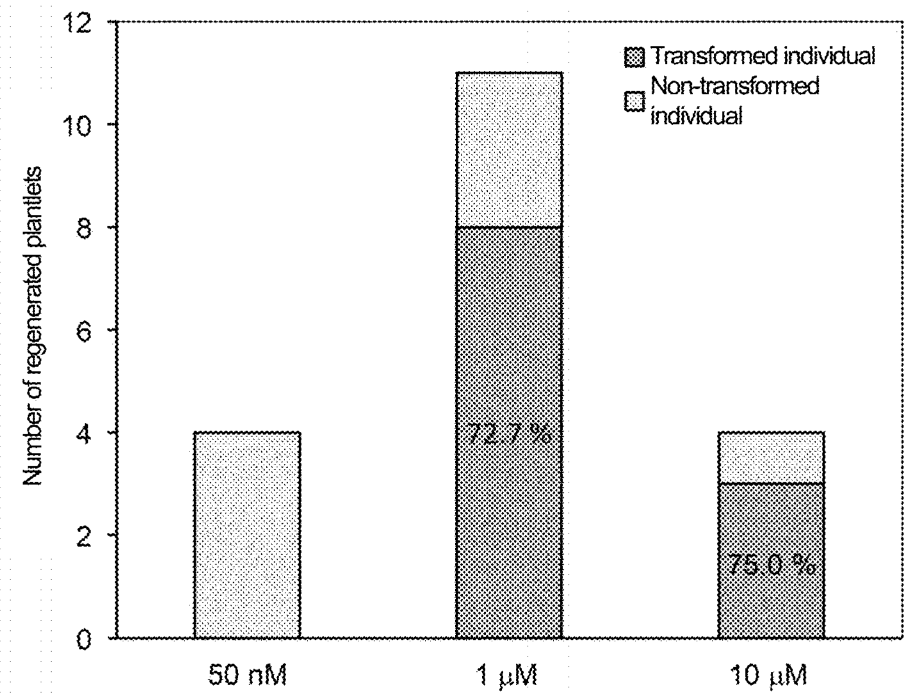
FIG. 12 is a graph showing the number of regenerated plantlets obtained by transforming hard-to-transform plant *Rorippa aquatica* in the presence of CAP peptide. The horizontal axis indicates the concentration of CAP peptide. The value in the graph indicates the percentage of transformed individuals. n=15

The results are shown in FIG. 12. As a result, the addition of 1 μM CAP peptide resulted in high efficiency transformation (FIG. 12).

Test Example 9

Cherry tomato Sun Cherry seedlings were purchased, sprayed with 1 μM CAP peptide on Jul. 21, 2021, and then grown in planters in an alley. The second 1 μM CAP peptide treatment was performed on July 28.

Figure 13:
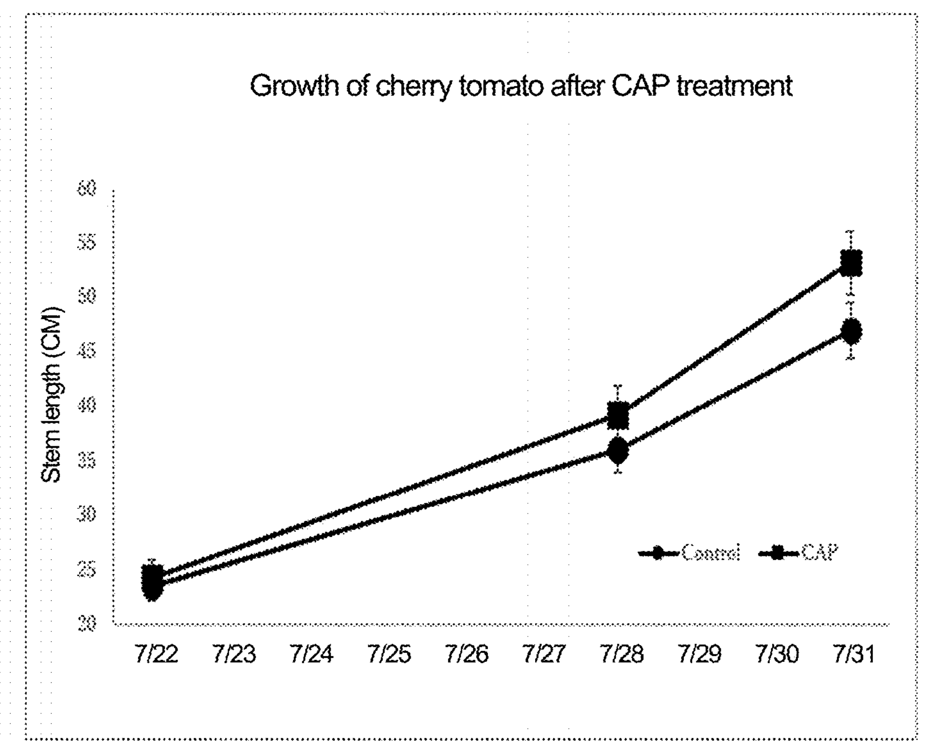
FIG. 13 is a graph showing the effect of promoting growth by treating cherry tomato Sun Cherry seedlings with CAP peptide. The values in the graph are mean±SD, and n=4 (control), 5 (CAP peptide treatment).

The results are shown in FIG. 13. As a result, compared with the CAP-untreated group, the effect of promoting stem extension was significantly confirmed (t-test: $p<0.05$) in the CAP-treated group only on July 3 after the 1 μM CAP peptide treatment was performed twice (FIG. 13).

The invention claimed is:

1. An agent comprising:

a peptide consisting of an amino acid sequence of a conserved region of cysteine-rich secretory protein, antigen 5, and pathogenesis-related 1 (CAP), wherein:

the amino acid sequence of the conserved region comprises an amino acid sequence represented by formula (I):

$$(X^1)_n TQX^2X^3W \quad (I)$$

wherein:

(i) $X^1$ represents phenylalanine or tyrosine, $X^2$ represents isoleucine or valine, $X^3$ represents isoleucine or valine, and n represents 0 or 1;

(ii) $X^1$ represents phenylalanine, $X^2$ represents isoleucine or valine, $X^3$ represents isoleucine or valine, and n represents 1; or (iii) $X^1$ represents phenylalanine or tyrosine, $X^2$ represents isoleucine or valine, $X^3$ represents isoleucine or valine, and n represents 0 or 1, and the amino acid sequence has at least 95% sequence identity to SEQ ID NO: 1, and the amino acid sequence has 39 or less amino acid residues, and the peptide has at least one effect selected from the following effects:

a plant stem cell-inducing effect, a plant environmental stress tolerance-enhancing effect, a plant pest resistance-inducing effect, a germination-promoting effect, a plant transformation efficiency-enhancing effect, and a plant growth-promoting effect; and at least one additive selected from the group consisting of a surfactant, a wetting agent, a stabilizer, and a penetrant.

2. A plant stem cell inducer comprising the agent according to claim 1.

3. A plant environmental stress tolerance enhancer comprising the agent according to claim 1.

4. A plant pest resistance inducer comprising the agent according to claim 1.

5. A germination promoter comprising the agent according to claim 1.

6. A plant transformation efficiency enhancer comprising the agent according to claim 1.

7. A plant growth promoter comprising the agent according to claim 1.

8. A method for producing plant stem cells, comprising applying the agent according to claim 1 to a plant body.

9. A method for enhancing the environmental stress tolerance of a plant body, comprising applying the agent according to claim 1 to the plant body.

10. A plant pest control method comprising applying the agent according to claim 1 to a plant body.

11. A method for promoting plant seed germination, comprising applying the agent according to claim 1 to plant seeds.

12. A method for transforming a plant body, comprising transforming the plant body in the presence of the agent according to claim 1.

13. A method for promoting the growth of a plant body, comprising applying the agent according to claim 1 to the plant body.

14. The agent according to claim 1, wherein the amino acid sequence of the conserved region has 25 or less amino acid residues.

15. The agent according to claim 1, wherein the peptide has at least one effect selected from the following effects:

a plant environmental stress tolerance-enhancing effect, a plant pest resistance-inducing effect, and a plant growth-promoting effect.

16. The agent according to claim 1, wherein the peptide has a plant environmental stress tolerance-enhancing effect selected from the group consisting of:

a drought tolerance-enhancing effect, an osmotic tolerance-enhancing effect, a salt tolerance-enhancing effect, and a freezing tolerance-enhancing effect.

17. The agent according to claim 1 further comprising at least one selected from the group consisting of a support, a preservative, a binder, a coloring agent, an emulsifier, a dispersant, a thickener, and an antifoaming agent.

18. The agent according to claim 1, wherein the at least one additive is a stabilizer.

19. The agent according to claim 1, wherein the at least one additive is a penetrant.

* * * * *